(12) United States Patent
Friggeri et al.

(10) Patent No.: US 8,956,656 B2
(45) Date of Patent: *Feb. 17, 2015

(54) PRODUCTION OF SMALL PARTICLES

(75) Inventors: Arianna Friggeri, Groningen (NL); Kjeld Jacobus Cornelis van Bommel, Groningen (NL); George Thomas Robillard, Zuidhorn (NL)

(73) Assignee: Nano Fiber Matrices B.V., Groningen (NL)

( * ) Notice: Subject to any disclaimer, the term of this patent is extended or adjusted under 35 U.S.C. 154(b) by 2685 days.

This patent is subject to a terminal disclaimer.

(21) Appl. No.: 11/284,804

(22) Filed: Nov. 22, 2005

(65) Prior Publication Data

US 2006/0099270 A1 May 11, 2006

Related U.S. Application Data

(63) Continuation of application No. PCT/NL2004/000350, filed on May 19, 2004.

(30) Foreign Application Priority Data

May 22, 2003 (NL) .................. PCT/NL03/00381
Nov. 12, 2003 (EP) .................... 03078600

(51) Int. Cl.
*A61K 9/14* (2006.01)
*A61K 9/10* (2006.01)
*C08J 3/075* (2006.01)
*C07D 215/38* (2006.01)
*A61K 9/16* (2006.01)
*B01J 2/08* (2006.01)

(52) U.S. Cl.
CPC ............ *C07D 215/38* (2013.01); *A61K 9/14* (2013.01); *A61K 9/1688* (2013.01); *B01J 2/08* (2013.01); *Y10S 977/906* (2013.01)
USPC ............ 424/489; 424/499; 516/103; 977/906

(58) Field of Classification Search
None
See application file for complete search history.

(56) References Cited

U.S. PATENT DOCUMENTS

| | | | |
|---|---|---|---|
| 4,522,743 A | 6/1985 | Horn et al. | |
| 4,937,081 A | 6/1990 | Kagotani | |
| 5,091,443 A * | 2/1992 | Karakelle et al. | 424/665 |
| 5,145,684 A | 9/1992 | Liversidge et al. | |
| 5,700,331 A * | 12/1997 | Thomas et al. | 134/29 |
| 6,048,550 A * | 4/2000 | Chan et al. | 424/497 |
| 6,096,710 A * | 8/2000 | Goodman et al. | 514/17 |
| 6,180,096 B1 | 1/2001 | Kline | |
| 6,372,235 B1 * | 4/2002 | Livoreil et al. | 424/401 |
| 7,645,805 B2 * | 1/2010 | van Bommel et al. | 516/103 |
| 2003/0013799 A1 | 1/2003 | Crooks et al. | |
| 2003/0041602 A1 | 3/2003 | Williams, III et al. | |
| 2005/0272677 A1 * | 12/2005 | Friesen et al. | 514/44 |

FOREIGN PATENT DOCUMENTS

| | | |
|---|---|---|
| EP | 1 631 261 B1 | 5/2004 |
| JP | 3901709 | 4/2007 |
| WO | WO9323008 | 11/1993 |
| WO | WO0247659 | 6/2002 |
| WO | WO 02/078674 | 10/2002 |
| WO | WO03032951 | 4/2003 |
| WO | WO03059319 | 7/2003 |
| WO | WO03084508 | 10/2003 |
| WO | WO03097587 | 11/2003 |
| WO | WO 2004/103347 | 12/2004 |
| WO | WO2004103347 | 12/2004 |

OTHER PUBLICATIONS

Hanabusa, K., et al., "Small molecular gelling agents . . . ", 1997, Chemistry Letters, pp. 191-192.*
Lochhead, R.Y. et al., "Appendix: Encyclopedia of Polymers and Thickeners for Cosmetics", 1999, Marcel Dekker, Inc., pp. 1-85.*
"Gellants-Paints", http://alalliancechem.com/GellantsPaints01.html, accessed Mar. 25, 2011.*
Auweter et al., "The Function of Gelatin in Controlled Precipitation Processes of Nanosize Particles," J. Dispersion Science and Technology, 1998, pp. 163-184, vol. 19.
Sugimoto et al., "Synthesis of uniform anatase $TiO_2$ nanoparticles by gel-sol method 3. Formation process and size control," Journal of Colloid and Interface Science, 2003, pp. 43-52, vol. 259.
PCT International Search Report, PCT/NL2004/000350, dated Jan. 20, 2005.
Heeres et al., Orthogonal Self-Assembly of Low Molecular Weight Hydrogelators and Surfactants, J. Am. Chem. Soc., 2003, pp. 14252-14253, vol. 125, No. 47, US.
PCT International Preliminary Report on Patentability, PCT/NL2004/000350, dated Sep. 2, 2005.
Sivtsov et al., Determination of the Molecular-Weight Characteristics of Polyacrylic Acid and Its Copolymer with Butyl Acrylate, Russian Journal of Applied Chemistry, 2010, pp. 728-731, vol. 83. No. 4.

* cited by examiner

*Primary Examiner* — Michael G Hartley
*Assistant Examiner* — Lance Rider
(74) *Attorney, Agent, or Firm* — TraskBritt, P.C.

(57) ABSTRACT

The present invention relates to a method for producing particles of a compound of interest. In a method according to the invention a solution is provided of the compound of interest in a solvent. This solution is thickened or gelled and particles are formed. The invention further relates to a particle that is obtainable by the invention.

36 Claims, 6 Drawing Sheets a  b  c  d a b c a	b	c

PRODUCTION OF SMALL PARTICLES

CROSS-REFERENCE TO RELATED APPLICATIONS

This application is a continuation of PCT International Patent Application No. PCT/NL2004/000350 filed on May 19, 2004, designating the United States of America, and published in English, as PCT International Publication No. WO 2004/103347 A2 on Dec. 2, 2004, which application claims priority to PCT/NL03/00381, filed on May 22, 2003 and EP 03078600.8 filed on Nov. 12, 2003, the contents of the entirety of each of which are incorporated herein by this reference.

FIELD OF THE INVENTION

Various embodiments of the present invention generally relate to biotechnology.

BACKGROUND OF THE INVENTION

The invention relates to a method for producing small particles and to the small particles obtainable thereby. The invention particularly relates to the production of small particles of biologically or pharmaceutically active compounds which are poorly soluble in water.

High bioavailability and short dissolution times are desirable characteristics for products, such as pharmaceuticals. However, many pharmaceutical products (or lead compounds developed in drug discovery) are highly hydrophobic and therefore poorly soluble in water. Such poor solubility in water is therefore a limit to their bioavailability and thus a limit to their effectiveness as drugs.

It is known that the rate of dissolution of a particulate product, such as a drug, depends on the size of the particles of that product and that dissolution can increase by increasing the surface area of the particles, e.g. by decreasing the particle size. Furthermore, it is also known that different crystalline polymorphs of a product such as a drug can dissolve at a different rate and that amorphous particles dissolve faster than their crystalline equivalents.

Some of the methods developed to solve the problem of poor solubility of drugs involve: milling techniques (U.S. Pat. No. 5,145,684), spray freezing into liquid (US 2003/0041602 A1), template emulsions WO 03/059319 A1), evaporation precipitation WO 02/47659 A2). Milling techniques exhibit problems of contamination from the grinding media, also the drug is exposed to excessive shear and high temperatures that can cause the drug to decompose, amounts of drug may be lost during the process and large amounts of the drug are usually necessary. Spray freezing into liquid requires the use of a cryogenic liquid, excipients or stabilizers and produces particles between 10 nm and 100 µm. Template emulsions require the presence of emulsifiers and stabilizers, they also need to be prepared in the presence of solvents which have to be removed before any in vivo application, and produce particles between 0.2 and 20 µm. In the evaporation precipitation technique an aqueous dispersion of drug is obtained, therefore, stabilizers are required. Moreover, for evaporation of the solvent temperatures of at least 50° C. are required; and the particles produced are between 50 nm and 20 µm.

WO 03/059319 describes a method of producing drug particles wherein use is made of an emulsion of a templating agent (typically an oil) in water. A mixture comprising the drug is added to the emulsion, preferably under agitation, and the drug migrates into the template droplets. Herein the size of the droplets determines the size of the drug particles. In the described Examples, the obtained particles typically have a diameter of several micrometers and only after redispersing the particles for a number of hours the particles disintegrate into smaller particles of several hundreds of nanometers.

The emulsion described in WO 03/059319 optionally comprises a stabilizer for stabilizing the emulsion droplets in the water phase. In this method, the stabilizer also inhibits crystal growth, aggregation and agglomeration of the drug particles. The emulsion may be used as such or the used liquids (water and organic phase) may be removed, thereby causing the drug to precipitate or crystallize, and form particles of which the size is controlled by the size of the template droplets. This method is rather complicated and requires large quantities of many additives for a relatively small amount of drug.

WO 03/032951 describes a large-scale process for preparing crystalline particles of a drug substance wherein a solution of a drug is added to an anti-solvent under mixing, thereby forming a particle slurry. A stabilizer may be used to prevent substantial growth of the drug particle. The particle slurry is preferably cooled (at less than 10° C.). The examples describe the preparation of particles with a diameter of several hundreds of nanometers. For the process relatively complicated equipment is required.

There remains a need for an alternative methodology for preparing particles of compounds, such as pharmaceuticals.

It has now been found that it is possible to prepare particles of a compound of interest—such as nano-particles (in particular particles with a number average diameter of 1-1000 nm)—from a solution by changing the viscosity of the solution in a specific way.

Accordingly, the present invention relates to a method for producing particles of a compound of interest comprising the steps of:
 providing a solution of the compound of interest in a solvent;
 inducing thickening or gelation of said solution using a thickener or gelator to produce a thickened solution or gel.

The formation of particles may occur by precipitation of the compound of interest upon thickening or gelation of the solution, i.e. together with thickening/gelation, or the formation of particles may occur at a later stage.

The precipitation may be effected upon drying of the thickened or gelated solution. Drying may be accomplished by solvent evaporation, freeze drying, spray drying or by centrifuging. For this manner of precipitation, freeze-drying has been found particularly suitable.

The present method can be carried out very rapidly, for instance formation of the particles, in particular relatively small particles (e.g. of less than 200 nm), can suitably be finished within less than about an hour, if so desired. More in particular, particle formation may be carried out within 2-15 min, even more in particular within 5-10 min, although longer or shorter processing times are feasible, if so desired.

A method according to the invention does not require operation at a high temperature or to operate the method under (active) cooling, in particular it may be operated at or around ambient temperature (e.g. 15-30° C.).

It is not required to operate the method under high shear. In fact the method may be carried out without any substantial shearing or other form of agitation.

The use of additives other than the solvent(s) and the thickener(s)/gelator(s) is not required. In particular the invention can very suitably be employed in the absence of particle growth/size stabilizers, emulsifiers, surfactants and the like.

Nonetheless, one may add one or more additives.

A stabilizer may be used to control the size of the particles. A stabilizer generally has the effect that particles prepared by precipitation in the presence of stabilizer maintain their size whereas particles prepared without a stabilizer may aggregate into larger particles.

The choice of stabilizer or stabilizers will depend upon the compound of interest. Examples of particle stabilizers include phospholipids, surfactants, polymeric surfactants, vesicles, polymers, including co-polymers and homopolymers and biopolymers, and/or dispersion aids. Other suitable stabilizers are described in detail in the Handbook of Pharmaceutical Excipients, published jointly by the American Pharmaceutical Association and The Pharmaceutical Society of Great Britain, the Pharmaceutical Press, 1986. Such stabilizers are commercially available and/or can be prepared by techniques known in the art.

Suitable stabilizers are further described in "Polymer Handbook" 3rd Edition edited by J. Brandrup and E. H. Immergut. Examples of suitable homopolymers and co-polymers include polyolefins and substituted polyolefins such as polyethylene, polypropylene, polybutene, polybutadiene, and chlorinated derivatives thereof; polyacrylates and polymethacrylates; polydisubstituted esters; polyvinyl ethers, chlorides, acetates, and carboxylate esters such as polyvinyl butyrate caprylate, laurate, stearate, benzoate; polystyrene; natural rubber and hydrochlorinated rubber; ethyl, butyl, and benzyl celluloses; cellulose esters; and combinations of these polymers. Other suitable polymers are those polymers which can also function as a surfactant, such as nonionic polyalkylene glycol/(poly) carboxylic acid compounds; A-B-A block-type surfactants; and high molecular weight esters of natural vegetable oils such as the alkyl esters of stearic and oleic acids. In addition to polymers, very hydrophobic small molecules, that is, hexadecane can be employed as well. Preferred stabilizers are those that are a part of the GRAS-list, that is, alkyl esters of stearic and oleic acids. Depending on the molecular weight or the degree of cross linking, the stabilizer can be in the physical state of a liquid or oil, or can be a solid.

The stabilizers may be employed in an amount from 0.1 to 90, preferably from 0.5 to 50 percent by weight of the dispersed phase.

In one embodiment, the stabilizer is a surfactant. Surfactants that can be advantageously employed herein can be readily determined by those skilled in the art and include various nonionic, anionic, cationic, and amphoteric surfactants, or a blend of those surfactants.

Suitable surfactants include gelatin, casein, lecithin, phosphatides, gum acacia, cholesterol, tragacanth, fatty acids and fatty acid salts, benzalkonium chloride, glycerol mono and di fatty acid esters and ethers, cetostearyl alcohol, cetomacrogol 1000, polyoxyethylene castor oil derivatives, polyoxyethylene sorbitan fatty acid esters, for example, the commercially available Tweens, polyethylene glycols (including solid PEGs, e.g. having an Mw of more than 400 g/mol), poly (ethylene oxide/propylene oxide) copolymers, for example, the commercially available Poloxomers or Pluronics, polyoxyethylene fatty acid ethers, for example, the commercially available Brijs, polyoxyethylene fatty acid esters, sorbitan fatty acid esters, for example, the commercially available Spans, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropyhnethylcellulose, noncrystalline cellulose, magnesium aluminum silicate, triethanolamine, polyvinyl alcohol (PVA), sodium lauryl sulfate, polyvinylpyrrolidone (PVP), poly (acrylic acid), and other anionic, cationic, zwitterionc and nonionic surfactants.

Examples of nonionic surfactants include the polyalkylene glycol ethers and condensation products of aliphatic alcohols, aliphatic amines, or fatty acids with ethylene oxide or propylene oxide; polyvinyl alcohols of different molecular weights and degree of hydrolyzation; polyvinyl pyrrolidones; and the surfactants of the Brij, Tween, and Span series. Anionic surfactants include salts of alkyl aryl sulphonic acids, sulphated polyglycol ethers, and ethers of sulphosuccinic acid. Cationic surfactants include quaternary ammonium compounds and fatty amines. If used, the surfactant is generally employed in an amount of from 0.1 to 15%, more preferably from 2 to 10, % by weight of the total composition.

Additional excipients can be included, in particular in case the compound of interest is a pharmaceutical. These can be added before or after the particles of the compound of interest are formed, in order to enable the particles to be homogeneously admixed for appropriate use (such as administration). Suitable excipients include polymers, absorption enhancers, solubility enhancing agents, dissolution rate enhancing agents, bioadhesive agents, and controlled release agents.

Suitable excipients are described in detail in the Handbook of Pharmaceutical Excipients, published jointly by the American Pharmaceutical Association and The Pharmaceutical Society of Great Britain, the Pharmaceutical Press, 1986. Such excipients are commercially available and/or can be prepared by techniques known in the art.

It has been found that a method according to the invention can be carried out using simple equipment, e.g. as simple as glass vials and pipettes.

In addition, although a method according to the invention is suitable to be employed for large batches it can very suitably be carried out with relatively small amounts of the compound of interest, in particular for batches of about 100 mg or less, more in particular of about 10 mg or less. The batch size may even be down to about 1 mg or less. This advantage makes this method particularly interesting for finding out the effectiveness of new lead compounds of which only limited amounts are usually available or in case the compound of interest is very expensive and only limited amounts are required.

Further, the invention may be used to provide particles which demonstrate an improved bioavailability. In addition, particles obtainable in accordance with the invention may advantageously be employed in photography applications, cosmetics. In particular in sun screens, glitter products and the like, the particles may very suitably be employed in the form of a dispersion in the gel, in which they are stabilized.

A method according to the invention has been found particularly suitable to prepare particles with a relatively small size. It has been found possible to prepare a particulate material with a number average diameter of less than about 500 nm, in particular of less than about 300 nm, more in particular of less than about 100 nm, although it is also possible to prepare larger particles, e.g. up to 100 μm.

The lower limit of the particle size is determined by the molecular size of the compound of interest and may thus be less than 1 nm. For practical reasons, the number average particle size is preferably at least 1 nm, more preferably at least 10 nm.

The invention provides a highly suitable method for preparing amorphous or crystalline solid particles. Amorphous particles are desirable because amorphous particles generally exhibit a faster dissolution rate than crystalline particles of the same composition.

BRIEF DESCRIPTION OF THE SEVERAL
VIEWS OF THE DRAWINGS

FIG. 1 shows transmission electron microscopy pictures (TEM) of gels of cHexAm(PheAQ)(CH$_2$CH$_2$OCH$_2$ $CH_2OH)_2$ containing pyrene in a 1:1 molar ratio ($6.0\times10^{-3}$ mmol), in DMSO/H$_2$O (100 μL/900 μL), examined after 7 days, 18 days, 1 month and 2 months, respectively, from left to right FIG. 2 shows TEM pictures of cHexAm(PheAQ) (CH$_2$CH$_2$OCH$_2$CH$_2$OH)$_2$ and pyrene in a 1:1 molar ratio ($6.0\times10^{-3}$ mmol), in DMSO/1N HCl (100 μL/900 μL), examined after 7 days, 18 days, 1 month and 2 months, respectively, from left to right.

Figure 1:
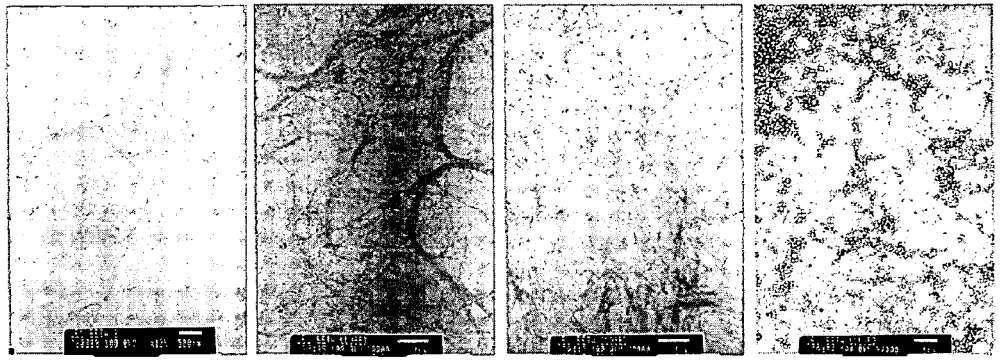

A compound used in accordance with the invention can in principle be any compound that can precipitate from a solution. It is noted that when referred to a compound of interest or a gelator/thickener, this is meant to include any protonated or deprotonated form of the compound, respectively the gelator/thickener. Thus, a compound respectively gelator/thickener in basic form used as a raw material may become protonated in the method, such that the particles contain (some of) the compound respectively the gelator/thickener in an acidic form or vice versa.

The invention has been found very suitable to prepare particles of a compound having a poor solubility in water. In this context a poor solubility in water means in particular that the solubility is less than 10 mg/ml at 20° C.

Preferably, the compound of interest is selected from the group consisting of pharmaceuticals, peptides, nucleic acids, proteins, enzymes, growth factors, steroids, hormones, antibiotics, gene therapy agents, catalysts, adsorbents, pigments, coatings, personal care products (including cosmetics), abrasives, particles for sensors, metals, alloys, ceramics, membrane materials, nutritional substances, anti-cancer agents, fertilizers, pesticides, herbicides, and combinations thereof.

Very good results have been achieved with a method wherein the compound of interest is a biologically or pharmaceutically active compound.

Preferably, the compound is selected from the groups of organic compounds, including metallo-organic compounds and organo-metallic compounds, e.g. cis-platinum complexes.

As a thickener, any agent may be used that is suitable to increase the viscosity of the solvent.

As a gelator, any agent may be used that is suitable to form a gel in combination with the solvent. The term gel is generally recognized in the art. A gel is usually defined as such when, upon inversion of the container in which it has been prepared, no immediate flow of liquid is observed.

Suitable thickeners and gelators are known in the art and include gelatine, starches and derivatives thereof, cellulose and derivatives thereof, gums, sorbitol, amino acid derivatives, such as N,N'dibenzoyl-L-cysteine, steroid derivatives and sugar derivatives.

Very suitable thickeners respectively gelators for use in accordance with the invention are low molecular weight thickeners respectively low molecular weight gelators, in particular those having a molecular weight of less than about 5000 g/mol, more in particular a molecular weight of about 100 to 2000 g/mol.

Highly suitable are organo-gelators as described in "Specialist Surfactants" edited by D. Robb of 1997, p 209-263, chapter 8 by P. Terech. In particular the hydroxylated carboxylic fatty acids with a linear or branched aliphatic carbon chain containing in particular at least 8 carbon atoms and preferably at least 12 carbon atoms, such as 12-hydroxystearic acid or 12-hydroxyoleic acid and their salts with alkali metals or alkaline earth metals; the amides of carboxylic acids, in particular tricarboxylic such as the cyclohexane tricatboxamides, resulting from the reaction of cyclohexane tricarboxylic acid and a lauryl amine; ureido derivatives such as the derivatives of 1,2-bis(ureido-)benzene and trans-1,2 bis(ureido)cyclohexane and in particular those described in the article. by R. M. Kellogg, B. L. Feringa et al in Chem Eur. J. 1999.5 . No. 3); the esters or amides of valine, and in particular those described in "Specialist Surfactants" (see above); the N-acyl amino acids and derivatives, and in particular the amides of N-acylamino acids such as the diamides resulting from the reaction of an N-acylamino acid with amines containing 1-22 carbon atoms, e.g. those described in WO 93/23008 and in particular the amides of N-acylglutamic acid where the acyl group represents a C8-C22 alkyl chain; the diamides having 1-22 carbon atoms, and preferably 6-18 carbon atoms, the hydrocarbon chains optionally substituted by ester, urea, fluoro groups (See French application no. 009317); amines or amides of steroids and particularly of deoxycholic, cholic, apocholic, lithocholic acids and their salts such as D-17,17-dipropyl-17a-aza-5-homoandrostan-3β-ol 17a-oxy or D-17,17-dipropyl-17a-aza-5-homoandrostan-3β-ol; compounds with several aromatic rings and in particular anthryl derivatives containing at least two alkyl chains having 8-30 carbon atoms such as 2,3-bis-n-decycloxyanthracene, 2,3-bis-n-decycloxyanthraquinon or containing a steroid group such as cholesteryl 4-(2-anthryloxy) butanoate or cholesteryl anthraquinon-2-carboxylaat and their derivatives; the azobenzene steroids such as those described in the book "Specialist Surfactants"; organo-metallic compounds such as mononuclear copper-β-diketonate (the complex of copper octa-substituted with bis(3,4 nonyloxybenzoyl) methanes), the binuclear copper tetracarboxylates or the complexes of Zn(II) with trisubstituted para-carboxyphenyl porphyrin; the surface active agents in the form of salts containing at least two linear or branched alkyl chains and in particular the alkyl phosphates of alkali metals or aluminium containing two alkyl chains having 8-30 carbon atoms such as the aluminium salt of dihexadecyl phosphate (C16) or di(2-ethyl hexyl) sulfosuccinic acid and its alkali metal salts (Na); the benzylidene sorbitols or alditols and derivative such as 1,3:2,4-di-o-benzylidene-D-sorbitol, and their mixtures.

Good results have been achieved with a gelator/thickener represented by the following formula

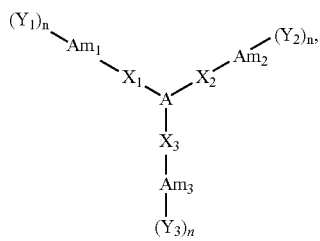

wherein

A represents a cycloalkyl, a heterocycloalkyl, an aromatic or heteroaromatic moiety;

each of $X_1$, $X_2$ and $X_3$ is independently chosen from the moieties —N(H)—, —C(O)—, —O(CO)—, —OC(S)—, —C(S)—, —NHC(S)— and —NH—C(O)—;

each of $Am_1$, $Am_2$, and $Am_3$ is independently a moiety based on an amino acid or a derivative thereof, or a number of amino acids or derivatives thereof;

each of $Y_1$, $Y_2$, and $Y_3$ is preferably independently chosen from the group of —OR, —N(OH)R, and —$NR_2$, if the corresponding X ($X_1$ for $Y_1$, $X_2$ for $Y_2$, and $X_3$ for $Y_3$) is —C(O)— or —NH—C(O)— and n=1, and each of $Y_1$, $Y_2$, and $Y_3$ is independently chosen from the group of —C(O)R, —C(O)—$NR_2$, —C(O)—OR, —C(S)R, —C(S)—$NR_2$, —C(S)—OR and R, if the corresponding X ($X_1$ for $Y_1$, $X_2$ for $Y_2$, and $X_3$ for $Y_3$) is —NH— and n=1 or 2, wherein each R is independently H, or a substituted or unsubstituted, branched, cyclic or straight alkyl, alkenyl or alkynyl group which possibly contains an aromatic, ester or ether moiety or one or more other heteroatoms—preferably selected from O, N, P, S and B—and may have from 1 to 40 carbon atoms; and n is 1 or 2.

In case A is a (hetero)cycloalkyl, all shown substituents (each X—Am—Y group) are preferably in the equatorial position of the (hetero)cycloalkyl core.

The preparation of a compound according to Formula I and preferred examples of such compounds are known from International application number PCT/NL03/00381 or European application number 02077007.9, the contents of which are incorporated herein by reference.

In the context of the invention, a cycloalkyl group is defined as a saturated or unsaturated cyclic alkyl group having from 4 to 18 carbon atoms. Preferred are cycloalkyl groups comprising 5- or 6-membered rings, in particular cyclopentyl, cyclopentadienyl or cyclohexyl groups. It is to be noted that also annulated multiple ring systems are encompassed by the term cycloalkyl group. Examples are decahydronaphtalene, dodecahydrophenalene, and hexadecahydropyrene.

A heterocycloalkyl group is defined as a saturated or unsaturated cyclic alkyl group having one or more heteroatoms (i.e. atoms other than carbon atoms) in the ring. The heterocycloalkyl group preferably comprises one or more fused or coupled 4- to 16-, more preferably 5- or 6-membered rings. Preferred heteroatoms that can be present in the ring are oxygen, sulphur and nitrogen. If present at all, it is preferred that one, two or three heteroatoms are present in the ring. These may be the same or different. It is to be noted that also annulated multiple ring systems are encompassed by the term heterocycloalkyl group. Examples are tetrahydropyran, tetrahydrothiopyran, dioxane, trans-hexahydro-isochroman, and trans-hydro-isothiochroman.

An aromatic group is defined as a cyclic group having an aromatic character comprising from 6 to 18 carbon atoms wherein the ring system(s) only contains carbon atoms. It is to be noted that also fused or coupled multiple ring systems are encompassed by the term aromatic group. Examples are phenyl, naphthyl, anthracyl, and pyrene. Preferably the trisubstituted aromatic ring is a trisubstituted benzene ring.

A heteroaromatic group is an aromatic group wherein one or more carbon atoms in a ring have been replaced by a heteroatom.

Preferred heteroatoms that can be present in the ring are oxygen, sulfur and nitrogen. It is preferred that one, two or three heteroatoms are present in the ring. These may be the same or different. It is to be noted that also fused or coupled multiple ring systems are encompassed by the term heteroaromatic group. Examples are furan, pyridine, pyrazine, quinoline, and thiophene.

Very suitable as a gelator/thickener in a method according to the invention is a non-symmetrical trisubstituted cyclic thickener or gelator, of which the ring is substituted by one or two X—Am—$Y_n$ groups and wherein the remaining one or two substituents are —X-Z groups, wherein each of X is independently chosen from the moieties —N(H)—, —C(O)—, —O(CO)—, —OC(S)—, —C(S)—, —NHC(S)— and —NH—C(O)—;

each of Am is independently a moiety based on an amino acid or a derivative thereof, or a number of amino acids or derivatives thereof;

each of Y is independently chosen from the group of —OR, —N(OH)R, —$NR_2$, —C(O)R, —C(O)—$NR_2$, —C(O)—OR, —C(S)R, —C(S)—$NR_2$, —C(S)—OR and R, wherein each R is independently H, or a substituted or unsubstituted, branched, cyclic or straight alkyl, alkenyl or alkynyl group which possibly contains an aromatic, ester or ether moiety or one or more other heteroatoms and may have from 1 to 40 carbon atoms;

each Z is independently selected from the group consisting of —OH, —COOH, —C(O)NHR, —NHC(O)R and —NHR, wherein each R is independently as defined above; and n=1 or 2.

Such a non-symmetrical trisubstituted thickener or gelator may be represented by one of the following formulas, wherein A represents the ring (core) of the thickener or gelator and each X, Y, Z respectively Am can represent the same or different X, Y, Z respectively Am.

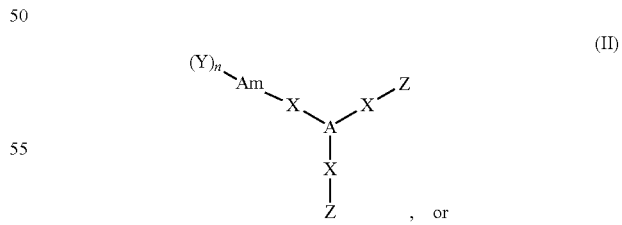

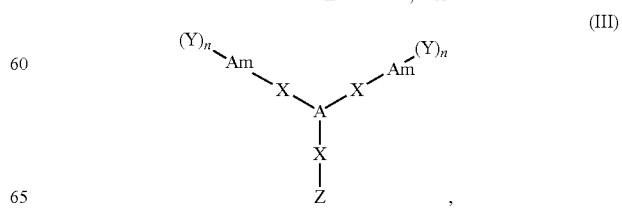

The term non-symmetrical is used herein to define that at least two of the substituents of the non-symmetrical trisubstituted gelator/thickener are different from each other; in particular the —X-Z group should be different from the —X—Am—$Y_n$ groups, in case the thickener or gelator contains two identical X—Am—$Y_n$ groups and the —X—Am—$Y_n$ should be different from the —X-Z groups in case the thickener or gelator contains two identical —X-Z groups. Preferably, the thickener or gelator is non-symmetrical in the sense that at least one —X-Z group is present that does not represent any moiety which is represented by —X—Am—$Y_n$. More in particular, at least one of the substituents is preferably free of an Am group, as defined herein.

The three substituents of the trisubstituted thickener/gelator are preferably distributed essentially evenly around the ring structure, i.e. in a six-membered ring the ring is preferably a 1,3,5 substituted ring.

The substituted ring in the non-symmetrical trisubstituted thickener/gelator may be a cycloalkyl, a heterocycloalkyl, an aromatic or heteroaromatic moiety. Very good results have been achieved with a thickener or gelator wherein the trisubstituted ring is formed by only carbon atoms.

In case of a (hetero)cycloalkyl, the substituents are preferably all in the equatorial position (i.e. in case of a gelator/thickener with a cyclohexyl core the compound has a "cis, cis"-configuration).

Preferably the substituted ring is a six-membered ring, preferably a cyclohexane or a phenyl. More preferably the ring is a 1,3,5 substituted ring.

Each X in the non-symmetrical gelator/thickener may be the same or different. Accordingly, the Am and the Z groups can each independently be connected to A by attachment to a C═O or a NH group. The choice for each X in the X—Am—$Y_n$ group will depend on whether the respective Am groups are to be attached at their $NH_2$-terminus or their COOH-terminus. If an amino acid or oligopeptide is connected through its $NH_2$-terminus, the particular X will be —C(O)— or —NH—C(O)—. Likewise, if an amino acid or oligopeptide is connected through its COOH-terminus the particular X will be an NH group.

In a gelator/thickener according to formula I or a non-symmetrical gelator/thicker, such as shown in formula II or III, each Am group is based on an amino acid or a derivative thereof. In principle, any group comprising at least one —NH or —$NH_2$ group and at least one —COOH group is considered an amino acid. It will be understood that each Am does not represent a complete amino acid. The amino acids are connected either through their $NH_2$-terminus to a corresponding X group and through their COOH-terminus to a corresponding Y group, or vice versa. The connection may e.g. be an amide, urea, thioamide or a carbamate bond. Accordingly, one or two H-atoms of the $NH_2$-terminus, and the —OH of the COOH-terminus are not part of the overall structure.

It is also possible that any of the Am groups is based on more than one amino acid or a derivative thereof, and accordingly comprises a peptide, such as a di-, tri-, or oligopeptide. Preferably, each oligopeptide is based on up to 12, more preferably 2 to 5 amino acids, forming a linear peptide chain in which the amino acids are connected head-to-tail to one another. The amino acids may be chosen from all natural and unnatural (synthetic, e.g. β-amino acids or α-alkylated amino acids) amino acids. Preferably, the amino acids are α, β, or γ-amino acids, of which both the D and the L isomers are eligible. Particularly preferred are α-amino acids. Suitable examples of amino acids are leucine, isoleucine, lysine, valine, proline, methionine, glycine, histidine, alanine, phenylalanine, tryptophan, serine, threonine, cysteine, tyrosine, asparagine, glutamine, aspartic acid, glutamic acid, and arginine. Very good results have been achieved with a thickener or gelator wherein the Am group is based on phenylalanine or methionine. Another preferred Am group is based on cysteine. The presence of cystein residues may very suitably be used to form a cross-linked gel. After all, the —SH group in cystein residues can form a disulphide bridge that may suitably be used to form a cross-linked gel. In the context of the invention, a derivative of an amino acid is defined as to include esters or amides (e.g. of aspartic acid, lysine or glutamic acid) and (thio)ethers (e.g. of serine, tyrosine or cysteine).

Each amino acid may be substituted with a substituent, wherein each substituent may be a substituted or unsubstituted, branched, cyclic or straight alkyl or alkenyl group which possibly contains an aromatic, ester or ether moiety or one or more other heteroatoms chosen from the group of N, S, O, P and B. Preferably, each substituent does not contain more than 12 carbon atoms. Preferably, each of the Am groups contains none or one substituent.

In particular in case of a trisubstituted, non-symmetrical gelator or thickener, the end groups Y each may independently be chosen from the groups dependent on the nature of the corresponding X and the value of n. For instance, if X is —C(O)—, —C(S)—, —OC(O)—, —OC(S), —NH—C(O)—, or —NH—C(S)— and n=1, Y may be —OR, —N(OH)R, or —$NR_2$. If X is for instance —NH— and n=2, Y may be —C(O)R, —C(O)—$NR_2$, —C(O)—OR, —C(S)R, —C(S)—$NR_2$, —C(S)—OR or R. In the latter case, the two Y groups on the same X—Am—$Y_2$ may be interconnected by an R-group, not being H. Each of the R-groups mentioned in this regard, may be independently chosen from the group of H and substituted or unsubstituted, branched, cyclic or straight alkyl, alkenyl or alkynyl groups which possibly contain an aromatic, ester or ether moiety or one or more other heteroatoms and may have from 1 to 40 carbon atoms, and preferably has 12 carbon atoms or less. Very good results have inter alia been achieved with an R-group free of heteroatoms, such as with -naphthyl (—$C_{10}H_7$) or with —$CH_2$-phenyl (—$C_7H_7$).

If the R-group contains one or more heteroatoms, the heteroatoms are preferably chosen from O, N, S, P and B.

In particular, in a gelator/thickener according to formula I, each Y preferably is independently selected from —OH, —O—$(CH_2)_i$—OH, —$NH_2$, —$NH(CH_2)_i$—$O(CH_2)_j$OH, —$O(CH_2)_iO(CH_2)_j$OH, —NHOH, —$NH(CH_2)_i$OH. In said groups i, j preferably are each independently selected in the range of 1 to 8, more preferably each independently are 1 or 2. Very good results have been achieved with such a gelator/thickener, wherein the substituted ring is a substituted cyclohexane or substitute benzene.

Very good results have been achieved with a gelator/thickener—in particular a non-symmetrical gelator/thickener according to formulas II or III—wherein each Y is independently selected from —$OCH_3$, —$OCH_2CH_3$, —$NH(CH_2)_2OCH_2CH_3$, —$O(CH_2)_2OCH_2CH_3$, —NH-alk (wherein alk is an alkyl group), a naphthyl group, an —NH-naphthyl group, —NH—$(CH_2)$Ph, NH-Ph-OMe and NH-quinoline.

In particular a gelator/thickener according to formula I, II or III may be used in accordance with the invention, to form a gel or thickened solution comprising the compound of interest, which gelator/thickener has good mucoadhesive properties. Very good result in this respect have been achieved with such a gelator/thickener wherein Y is a —[(CH$_2$)$_k$—O—]$_l$(CH$_2$)$_m$—OH group. Such gelator/thickener has been found very advantageous for use in a method of preparing particles of a pharmaceutical that is intended for uptake via a mucus layer. Herein k, l, and m are integers, and preferably each independently 1 or 2, more preferably k and m are 2 while m is 1.

Such a gelator may advantageously be present in the pharmaceutical preparation in combination with the pharmaceutical compound of interest, because it has been found that a compound of interest shows increased bioavailability in combination with such a gelator. It is contemplated by the inventors that the improved uptake of the compound of interest might also derive from the good mucoadhesive properties of the gelator/thickener that contribute to adherence of the compound of interest to a mucus layer, e.g. via the nose or gastrointestinal tract.

In case the non-symmetrical thickener or gelator comprises two —X—Am—(Y)$_n$ groups, both —X—Am—(Y)$_n$ groups are preferably the same.

In an embodiment, a gelator/thickener according to the invention, in particular a gelator according to the invention contains a reactive group that can contribute to the gelling or thickening by forming cross-links. By choosing an appropriate reactive group, a gelling agent or thickener according to the invention may be used to form a gel or thickened solution which can be subjected to further reaction. Any of the Am, Z and/or Y may contain such a reactive group. Examples of reactive groups are —C═C— groups (e.g. in the R moiety of Y or Z) and —SH groups (e.g. in the Am moiety).

For instance, a gelling agent or thickener with a reactive group—e.g. a terminal alkenyl group (C═C)— can, after formation of a viscous solution or a gel, be interconnected by a metathesis reaction following standard procedures as found in e.g. *J. Am. Chem. Soc.* (1995) 117, 12364. The metathesis reaction transforms the viscous solution or gel into a (stiffer) gel, which can for instance be used in columns for chromatographic purposes (see also Sinner et al., *Angew. Chem. Int. Ed.* 39 (2000) 1433-1436 and Sinner et al., *Macromolecules* 33 (2000) 5777-5786).

Besides, it is possible to achieve the gelling or thickening by letting the reactive group react with a chemical, e.g. one may react a gelator/thickener according to the invention comprising a thiol group with a bis-maleimide or the like, to achieve gelling or thickening. Suitable reaction conditions are known in the art for known gelling agents and thickeners comprising such a reactive group suitable to achieve cross-linking. Suitable reaction conditions are known in the art for other cross-linking reactions.

The Z group in the non-symmetrical trisubstituted gelator/thickener may be a group as defined for Y. Preferably each X-Z is chosen independently from the group consisting of C(O)NHR or C(O)OR, wherein R is more preferably H or an alkyl, even more preferably H or —CH$_3$; —NHC(O)R; —NHR; —C(O)—NH—(CH$_2$)$_i$—OH, wherein i preferably is 1-8, for instance 2; —C(O)—NH—(CH$_2$)$_i$—O—(CH$_2$)$_j$—OH, wherein i, j are preferably 1-8, for instance 1 or 2; and —C(O)NH(CH$_2$)$_i$-pyr, wherein i preferably is 1, 2 or 3. Any of these X-Z groups have been found particularly suitable in case the substituted ring of the thickener or gelator is a substituted cyclohexane or substituted benzene. In a particularly preferred method of the invention the ring is a substituted cyclohexane.

In particular in case of a non-symmetrical 1,3,5-substituted cyclohexane very good results with respect to gelling or thickening have been achieved with a thickener or gelator wherein —X-Z is chosen from the groups of —COOH, —C(O)—NH$_2$, —C(O)—NHCH$_3$, —C(O)—NH—(CH$_2$)$_2$—OH, —C(O)—NH—(CH$_2$)$_2$—O—(CH$_2$)$_2$—OH and C(O)NHCH$_2$-pyr.

Typical methods of preparing a gelling agent or thickener according to Formula I will now be described with reference to six preferred groups of compounds. It will be understood by the skilled person that many variations in the synthesis are possible without leaving the scope of the invention.

Group 1

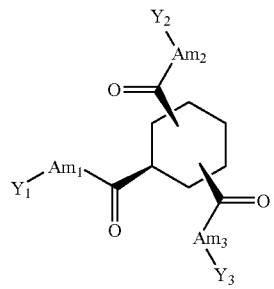

(◀ represents a substituent in an equatorial position of the cyclohexane core)

A thickener or gelling agent according to this formula can be prepared by reaction of a cyclohexanetricarboxylic acid with SOCl$_2$ (formation of the acyl chloride) and subsequent reaction (K. Hanabusa, A. Kawakima, M. Kimura, H. Shirai, *Chem. Lett* (1997) 191-192) with a free amino group of an amino acid derivative, such as an amino acid alkyl ester or amide or an amino acid glycol ester or amide (according to standard organic procedures for amide and ester formation [of amino acids] as described in a.o. M. Kunishama, C. Kawachi, J. Morita, K. Tereao, F. Iwasaki, S. Tani, Tetrahedron (1999) 13159-13170; M. B. Smith, J. March, *March's Advanced Organic Chemistry*, 2001, 5$^{th}$ edition, Wiley Interscience; E. Muller, O. Bayer, *Houben-Weyl, Methoden der Organischen Chemie, Synthesen von Peptiden*, Band XV/1 and 2, 1974, George Thieme Verlag; N. Yamada, K. Okuyama, T. Serizawa, M. Kawasaki, S. Oshima, *J. Chem. Soc., Perkin Trans.* 2, (1996) 2707-2713; H. Tamiaki, A. Kiyomori, K. Maruyama, *Bull. Chem. Soc. Jpn*, 66, (1993) 1768-1772; S. Bhattacharya, S. N. G. Acharya, *Chem. Mater.* (1999) 3121-3132).

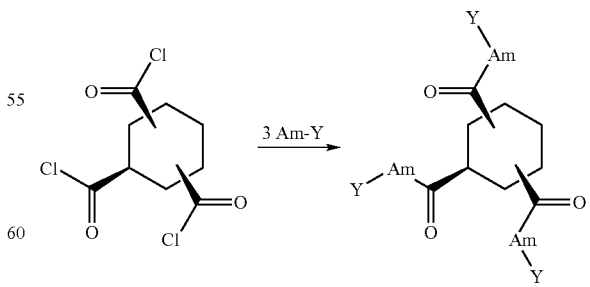

(◀ represents a substituent in an equatorial position of the cyclohexane core)

Y═OH can be prepared easily from Y═OR' by hydrolysis under alkaline conditions

Group 2

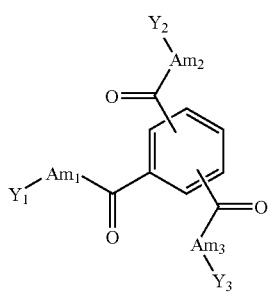

A thickener or gelling agent according to this formula can be prepared by reaction of a benzenetricarboxylic acid with $SOCl_2$ (formation of the acyl chloride) and subsequent reaction (K. Hanabusa, A. Kawakima, M. Kimura, H. Shirai, *Chem. Lett* (1997) 191-192) with a free amino group of an amino acid derivative, such as an amino acid alkyl ester or amide or an aminoacid glycol ester or amide.

Group 3

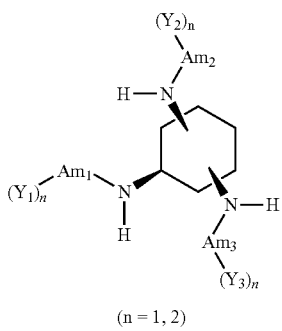

(◄ represents a substituent in an equatorial position of the cyclohexane core)

A thickener or gelling agent according to this formula can a.o. be prepared by reaction of a triaminocyclohexane (T. Bowen, R. P. Planalp, M. W. Brechbiel, *Bioorg. Med. Chem.*

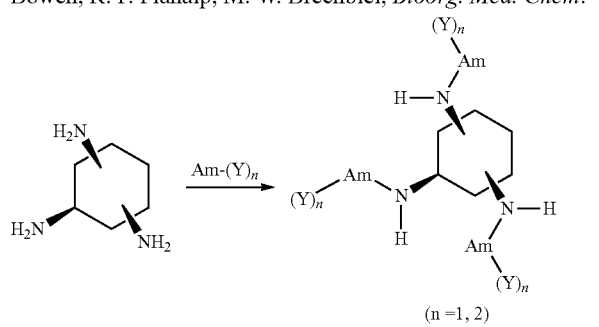

*Lett.* (1996) 807-810) with the free or activated carboxylic acid moiety of a) an amino acid protected at the N-terminus; e.g. NH(CO)—R (J. March, *March's Advanced Organic Chemistry*, 2001, 5$^{th}$ edition, Wiley Interscience; E. Muller, O. Bayer, *Houben-Weyl, Methoden der Organischen Chemie, Synthesen von Peptiden, Band* XV/1 and 2, 1974, George Thieme Verlag), NH(CO)OR(H-J. Knolker, T. Braxmeier, *Synlett*. (1997) 925-928, J. S. Nowick, D. L. Holmes, G. Noronha, E. M. Smith, T. M. Nguyen, S-L. Huang, *J. Org Chem.*, (1996) 3929-3934, I. Vauthey, F. Valot, C. Gozzi, F. Fache, M. Lemaire, *Tetrahedron Lett.* (2000) 6347-6350), S. Gasataldi, S. M. Weinreb, D. Stein, *J. Org. Chem.* (2000), 3239-3249, D. C. D. Butler, H. Alper, *Chem. Commun.* (1998) 2575-2576, P. Majer, R. S. Randad, *J. Org. Chem.*, (1994) 1937-1938, R. A. Batey, V. Santhakumar, C. Yoshinashi, S. D. Taylor, *Tetrahedron Lett.* (1998) 6267-6270, S. M. Hutchins, K. T. Capman, *Tetrahedron Lett.* (1995) 2583-2586.

b) an amino acid in which the free amine is reacted with an aldehyde (formation of an imine); N=C—R (J. March, *March's Advanced Organic Chemistry*, 2001, 5$^{th}$ edition, Wiley Interscience; E. Muller, O. Bayer, *Houben-Weyl, Methoden der Organischen Chemie, Synthesen von Peptiden*, Band XV/1 and 2, 1974, George Thieme Verlag).

Group 4

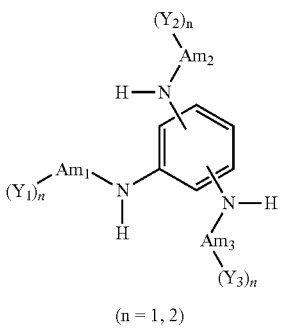

A thickener or gelling agent according to this formula can be prepared by reaction of a benzenetriamine (T. Yamaoka, H. Hosoya, S. Nagakura, *Tetrahedron* (1968) 6203-6213) with the free or activated carboxylic acid moiety of an amino acid derivative (see compounds of Group 3), or other simple C—N forming protocols (transition metal amination of aryl iodides) B. H. Yang, S. L. Buchwald, *Organometal. Chem.* (1999) 125-146, J. F. Hartwig, *Angew. Chem. Int. Ed. Engl.* (1998) 2046-2067.

Group 5

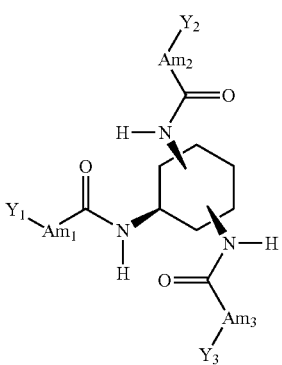

(◄ represents a substituent in an equatorial position of the cyclohexane core)

A thickener or gelling agent according to this formula can be prepared by activation of the triaminocyclohexane with phosgene, triphosgene, carbonyldiimidazole or (4-nitro)phenyl carbamate and subsequent reaction with a free amino group (G. T. Wang, Y. W. Chen, S. D. Wang, R. Sciotti, *Tetrahedron Lett.* (1997) 1895-1898, P. Majer, R. S. Randad, *J. Org Chem.*, (1994) 1937-1938, R. A. Batey, V. Santhakumar, C. Yoshinashi, S. D. Taylor, *Tetrahedron Lett.* (1998) 6267-6270, S. M. Hutchins, K. T. Capman, *Tetrahedron Lett.*

(1995) 2583-2586) of an amino acid derivative, such as an amino acid alkyl ester or amide or an amino acid glycol ester or amide. It is often assumed that the second step takes place via the formation of an isocyanate.

In another embodiment the cyclohexyl triisocyanate is formed in situ from the corresponding tricarboxylic acid azide by means of an Curtius rearrangement (C. F. H. Allen, A. Bell, *Organic Synthesis Collective Volume* 3, 6 ed. (1967) 846-847 and subsequently reacted with a free amino group of an amino acid derivative, such as an amino acid alkyl ester or amide or an amino acid glycol ester or amide.

In another embodiment the free amino group of an amino acid derivative is activated at first (in situ formation of the isocyanate, H. J. Knolker, T. Braxmeier, Synlett. (1997) 925-928 and subsequently reacted with triaminocyclohexane.

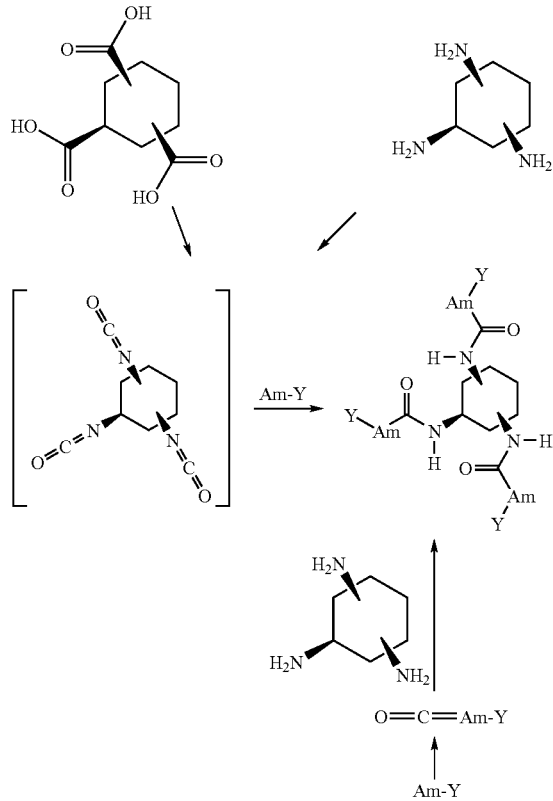

Group 6

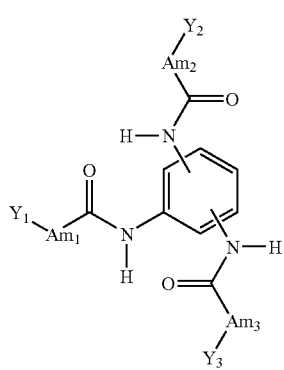

A thickener or gelling agent according to this formula can be prepared by reaction of a triaminobenzene with an isocyanate (in situ formed) of an amidated/esterified amino acid ((H-J Knolker, T. Braxmeier, *Synlett*. (1997) 925-928) or (in situ) formation of the triisocyanate (C. F. H. Allen, A. Bell, *Organic Synthesis Collective Volume* 3, 6 ed. (1967) 846-847, J. E. Gill, R. MacGillivray. J. Munro, *J. Chem. Soc.* (1949) 1753-1754) and subsequent reaction with three equivalents of the free amino group of an amino acid derivative, such as an aminoacid alkyl ester or amide or an aminoacid glycol ester or amide (see compounds 5).

Typical methods of preparing a non-symmetrical gelling agent or thickener, such as shown in Formula II or III, suitable for use in a method according to the invention will now be described with reference to two preferred groups of compounds. It will be understood by the skilled person that many variations in the synthesis are possible without leaving the scope of the invention. The skilled person will know how to prepare other gelators/thickeners based upon the information provided in the present description and claims and common general knowledge.

Group 1 of the Non-symmetrical Gelling Agents or Thickeners

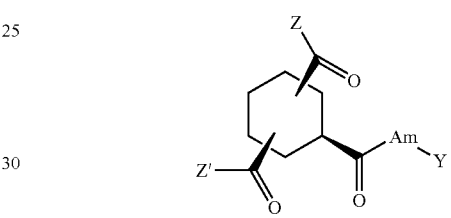

A thickener or gelling agent according to this formula (with $Z=Z'=OH$) can be prepared by reaction of a cyclohexanetricarboxylic acid, optionally after activation of the carboxylic acid group, with a free amino group of an amino acid derivative, such as an amino acid alkyl ester or amide, or an amino acid aryl ester or amide (according to standard organic procedures for amide and ester formation [of amino acids] as described in inter alia. M. Kunishama, C. Kawachi, J. Morita, K. Tereao, F. Iwasaki, S. Tani, *Tetrahedron* (1999) 13159-13170; M. B. Smith, J. March, *March's Advanced Organic Chemistry*, 2001, 5th edition, Wiley Interscience; E. Muller, O. Bayer, *Houben-Weyl, Methoden der Organischen Chemie, Synthesen von Peptiden*, Band XV/1 and 2, 1974, George Thieme Verlag; N. Yamada, K. Okuyama, T. Serizawa, M. Kawasaki, S. Oshima, *J. Chem. Soc., Perkin Trans*. 2, (1996) 2707-2713; H. Tamiaki, A. Kiyomori, K. Maruyama, *Bull. Chem. Soc. Jpn*, 66, (1993) 1768-1772; S. Bhattacharya, S. N. G. Acharya, *Chem. Mater*. (1999) 3121-3132). By using a large excess of the cyclohexanetricarboxylic acid in this reaction the formation of di- and tri-functionalized cyclohexanes can be limited. Isolation of the monoadduct can be accomplished by standard organic chemistry procedures, including crystallization/precipitation, column chromatography, extraction, etc.

Alternatively, a cyclohexanetricarboxylic derivative may be synthesized of which two of the carboxylic acid moieties are capped with protecting groups (e.g. converted to benzyl esters, but also other protecting groups may be used: see T. W. Greene, P. G. M. Wuts, *Protective groups in organic synthesis*, 1999, 3rd edition, Wiley Interscience). Reaction of the remaining carboxylic acid with a free amino group of an amino acid derivative (as described above), followed by removal of the protecting groups on the carboxylic acids (in the case of benzyl esters, $H_2$+Pd/C can be used. For the removal of other protective groups see T. W. Greene, P. G. M. Wuts, *Protective groups in organic synthesis*, 1999, 3$^{rd}$ edition, Wiley Interscience) then gives the monoadduct.

The thusly obtained monoadducts (with Z=Z'=OH) can be used for the formation of numerous derivatives by conversion of C(O)Z and/or C(O)Z' (with Z=Z'=OH) to give compounds in which Z and/or Z' are chosen from the group of —OR, NHR, NHC(O)R, wherein each R is independently chosen, and defined as above (other than R=H, which represents the monoadduct starting material). Such conversions can be carried out following standard organic procedures known to the person skilled in the art. Subsequent reaction steps may be carried out to further alter the structure of the compounds. An example of such a step is the hydrolysis (under alkaline conditions) of methyl esters of amino acids to give the corresponding free acids.

Group 2 of the Non-symmetrical Gelling Agents or Thickeners

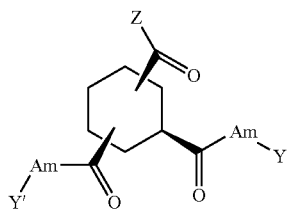

A thickener or gelling agent according to this formula (with Z=OH) can be prepared by reaction of a cyclohexanetricarboxylic acid, optionally after activation of the carboxylic acid groups, with a free amino group of an amino acid derivative, such as an amino acid alkyl ester or amide, or an amino acid aryl ester or amide (according to standard organic procedures for amide and ester formation [of amino acids] as described in a.o. M. Kunishama, C. Kawachi, J. Morita, K. Tereao, F. Iwasaki, S. Tani, *Tetrahedron* (1999) 13159-13170; M. B. Smith, J. March, *March's Advanced Organic Chemistry*, 2001, 5$^{th}$ edition, Wiley Interscience; E. Muller, O. Bayer, *Houben-Weyl, Methoden der Organischen Chemie, Synthesen von Peptiden*, Band XV/1 and 2, 1974, George Thieme Verlag; N. Yamada, K. Okuyama, T. Serizawa, M. Kawasaki, S. Oshima, *J. Chem. Soc., Perkin Trans.* 2, (1996) 2707-2713; H. Tamiaki, A. Kiyomori, K. Maruyama, *Bull. Chem. Soc. Jpn*, 66, (1993) 1768-1772; S. Bhattacharya, S. N. G. Acharya, *Chem. Mater*. (1999) 3121-3132). A mixture of mono, bis- and triadduct will be formed, from which the bisadduct can be isolated by standard organic chemistry procedures, including crystallization/precipitation, column chromatography, extraction, etc.

Alternatively, a thickener or gelling agent according to this formula (with Z=OH) can be prepared by using a cyclohexanetricarboxylic acid derivative of which one of the carboxylic acid moieties is capped with a protecting group (e.g. converted to a benzyl, but also other protecting groups may be used: see T. W. Greene, P. G. M. Wuts, *Protective groups in organic synthesis*, 1999, 3$^{rd}$ edition, Wiley Interscience). Reaction of the remaining carboxylic acids each with a free amino group of an amino acid derivative (as described above), followed by removal of the protecting group on the carboxylic acid (in the case of benzyl esters, $H_2$+Pd/C can be used. For the removal of other protective groups see T. W. Greene, P. G. M. Wuts, *Protective groups in organic synthesis*, 1999, 3$^{rd}$ edition, Wiley Interscience) then gives the bisadduct.

The thusly obtained bisadducts (with Z=OH) can be used for the formation of numerous derivatives by conversion of C(O)Z (with Z=OH) to give compounds in which Z is chosen from the group of —OR, NHR, NHC(O)R, wherein R is chosen, and defined as above (other than R—H which represents the bisadduct starting material. Such conversions can be carried out following standard organic procedures known to the person skilled in the art. Subsequent reaction steps may be carried out to further alter the structure of the compounds. An example of such a step is the hydrolysis (under alkaline conditions) of methyl esters of amino acids to give the corresponding free acids.

In particular with respect to a gelator/thickener comprising one —X—Am—$Y_n$ group and two —X-Z groups, a compound wherein Y is selected from NH-alkylene-phenyl (the alkylene preferably being methylene, ethylene or propylene), NH-phenyl-O-alkyl (the alkyl preferably being methyl, ethyl or propyl), —NH-naphthyl and —NH-quinoline has been found very suitable.

In particular with respect to a gelator/thickener comprising two —X—Am—$Y_n$ groups and one —X-Z group, a compound wherein Y is selected from O-alkyl and NH-alkyl, wherein the alkyl preferably is methyl, ethyl or propyl, —NH-alkylene-phenyl, —NH-phenyl-O-alkyl, —NH-naphthyl and —NH-quinoline has been found very suitable.

In the context of the invention, a derivative of an amino acid is defined as to include esters or amides (e.g. of aspartic acid, lysine or glutamic acid) and (thio)ethers (e.g. of serine, tyrosine or cysteine).

Each moiety Am in the above formula I, II or III, and in particular in the non-symmetrical 1,3,5-substituted cyclohexane or 1,3,5-substituted benzene compound is preferably independently selected from the group of leucine, isoleucine, lysine, valine, proline, methionine, glycine, histidine, alanine, phenylalanine, tryptophan, serine, threonine, cysteine, tyrosine, asparagine, glutamine, aspartic acid, glutamic acid, arginine, and derivatives thereof. Very good results have been achieved with phenylalanine or methionine. Another preferred amino acid is cysteine; such a compound according to the invention contains a cross-linkable —SH group, which is advantageous for the gelling/thickening properties of a gelling agent/thickener according to the invention.

As a solvent in principle any solvent can be used which allows the dissolution of the compound of interest and which can be thickened/gelated in the presence of the thickener/gelator (optionally in the presence of a gelling/thickening aid). Examples of suitable solvents include aromatic hydrocarbons, non-aromatic hydrocarbons, alcohols, ethers, esters, aldehydes, ketones, alkanoic acids, epoxides, amines, amides, for instance dimethylformamide (DMF), N-methylpyrrolidone (NMP), halogenated hydrocarbons, silicon oils, vegetable oils, phosphoric acids, sulfoxides, for instance dimethyl sulfoxide (DMSO), nitriles, water and mixtures thereof.

Particularly preferred solvents for solubility reasons are water, DMF, NMP, DMSO, ethanol (EtOH), acetonitrile ($CH_3CN$), propylene glycol (PG) and polyethylene glycol (PEG). The PEG may be any PEG that is liquid under the method conditions. Usually a PEG with an average molecular weight of less than or equal to about 400 g/mol will be used as a solvent.

Solvents, which are very interesting from a pharmaceutical point of view, are water, DMSO, NMP, PG, PEG and EtOH.

The solvents may be used in pure form, as mixtures, or may comprise additives, in particular one or more additives selected from the group consisting of salts, acids and bases, and the additives mentioned above, such as stabilizers, additional excipients and the like.

Examples of suitable acids include inorganic acids, in particular hydrogen halogenide (such as HCl). Examples of suitable bases include inorganic bases, in particular alkali-metal bases (such as NaOH). Examples of suitable salts include salts of said acids and bases.

As indicated above, in accordance with the invention a solution of the compound of interest is thickened or transformed into a gel by use of a thickener/gelator. In an embodiment of the invention, the thickening/gelling results in the precipitation of the compound of interest, thereby forming particles, although thickening/gelation need not be the cause of particle formation.

The concentrations and ratios of compound of interest, gelator/thickener, ratio of solvents, physical parameters such as temperature, precipitation time, agitation/shearing characteristics (if employed), addition velocity of a solvent, and pH can be used to obtain a particulate material with desirable characteristics. Suitable conditions can be determined by the skilled person, based upon common general knowledge and the information disclosed herein.

Dissolution of the compound of interest and/or the thickener may be facilitated by heating and/or sonication.

The temperature during thickening is usually not particularly critical and may suitably be between the melting temperature and boiling temperature of the solvent(s) used, with the proviso that the temperature is suitable to process the compound of interest and the thickener/gelling agent. For practical reasons the temperature is preferably between 0 and 300° C., more preferably between 10 and 40° C. Very good results have been achieved by operating at or around room temperature (about 20 to 30° C.).

A temperature higher than about 30° C. may be advantageously employed, in case a change in the temperature is used to cause thickening/gelation of the solvent or dissolution/thinning of the gel/thickened solution. Thus one may make use of elevated temperatures, as will be discussed in more detail below.

Gelation/thickening and/or formation of the particles may be effected with the aid of selecting a specific pH. The choice of such pH depends upon the solvent, compound of interest and gelator/thickener. Suitable conditions can be determined routinely with the help of the information disclosed herein. The pH change resulting in particle formation may be effected at any time. In particular in case the compound of interest is intended for oral administration (e.g. in case it is a pharmaceutical, a dietary supplement or a nutrient), particle formation may take place in the gastrointestinal tract after ingestion.

It is not necessary to agitate the solvent comprising the compound of interest before, during or after thickening or gelling or to subject it to shearing conditions. For practical reasons, some agitation/shearing may be performed, but it is in general preferred to carry out at least the gelation or thickening in the absence of any substantial mixing.

Several suitable manners of gelling/thickening are described now in some detail. The skilled person will appreciate that other possibilities exist and that the described embodiment may be adapted in various ways.

Gelation/Thickening by Solvent Effects

In an embodiment, gelator/thickener and compound of interest are dissolved in the same solvent or similar solvent.

In a suitable method gelator/thickener and compound or interest are dissolved in the same solvent. This solution is brought into contact with a different liquid, a so called non-solvent, i.e. a liquid wherein at least the gelator/thickener does not (fully) dissolve (under the relevant conditions such as pH, T, etc), leading to gelation or thickening. In particular, the thickener/gelator not being soluble in a liquid (such as the non-solvent) means herein that under the existing circumstances at least a substantial part of the gelator/thickener (in particular more than 50%, more in particular more than 90%) does not dissolve or does not remain dissolved.

Depending upon the non-solvent, the compound of interest may remain dissolved in the mixture of the solvent and the other liquid, in the form of cells/droplets entrapped in the gel/thickened solvent or it may (partially) precipitate, thereby forming solid particles. If not formed during gelling/thickening, solid particles of the compound of interest may be formed later, e.g. by drying, in particular by freeze-drying, if so desired.

In an embodiment the thickener/gelator and the compound of interest can interact electrostatically and give rise to salts (in case the gelator is acidic and compound of interest is basic or vice versa). In these cases, the concentration of the gelator is preferably in excess and the particles formed by addition of a non-solvent can be particles of the compound of interest, but also salt particles constituted of gelator and compound of interest. In such an embodiment the gelator may function as a stabilizer for the particles.

In an embodiment, first a solution of the thickener/gelator and a separate solution of the compound of interest are made. Then both solutions are contacted. The solvent of the solution of the compound of interest is chosen such that it is a non-solvent for the gelator/thickener, thereby causing the gelator/thickener to form a gel or thickened solution upon mixing both solutions.

Depending upon the solubility of the compound of interest in the mixture of the solvents, particle formation may be effected together with thickening/gelling or cells/droplets of the compound dissolved in the solvent mixture may be entrapped in the gel/thickened solvent mixture.

If not formed during gelling/thickening, solid particles of the compound of interest may be formed later, e.g. by drying, in particular by freeze-drying.

The use of different liquids to achieve dissolution of the gelator/thickener and the compound of interest and to effect gelation or thickening and optionally particle formation provides a wide variety of possibilities for the process, e.g. if the compound of interest and the gelator are not soluble in the same solvent, particle production will still be possible by using two different solvents. The second solvent may be miscible with the first or immiscible, i.e. forming a second liquid phase in the ratio of first to second solvent in which it is applied.

The induction of thickening or gelation may be realized by the presence of a solvent in which the gelator/thickener is essentially not soluble. This may be accomplished by choosing the solvent in which the compound of interest is dissolved such that the gelator/thickener is essentially not soluble. Alternatively, this may be accomplished by choosing a second solvent which is different from the solvent in which the compound of interest is dissolved as the solvent in which the gelator/thickener is essentially not soluble (the non-solvent).

This second solvent is then added to the solution wherein the compound of interest and the gelator or thickener are dissolved, upon which gelation or thickening occurs.

The skilled person will know how to choose suitable solvents and gelator or thickener depending upon the nature of the compound of interest, by common general knowledge and the information disclosed in the present description and claims. For instance the non-solvent may be an organic solvent, water (e.g. in the form of an aqueous solution) at a pH at which the drug and the gelator or thickener do not dissolve.

Gelation/Thickening by Temperature Effects

Gelation/thickening may be effected by changing the temperature from a temperature at which the gelator/thickener is dissolved in the solution to a temperature at which the gelator/thickener does not (fully) dissolve. Depending upon the type of gelator/thickener this may be achieved by raising or lowering the temperature. The skilled person will know how to determine whether gelling/thickening is effected by heating or by cooling. Generally, polymeric gelators tend to form gels upon heating, whereas low molecular weight-gelators/thickeners tend to dissolve at elevated temperature and tend to gelate/thicken upon cooling.

The temperature change may be effected by an external heating/cooling device.

For instance, in a suitable method, the thickener/gelator and the compound of interest are added to a liquid that does not (fully) dissolve the thickener/gelator and optionally the compound of interest at a low temperature. Then, the resultant mixture is heated until complete dissolution of the thickener/gelator (and compound of interest, if not dissolved already at a low temperature). This solution is then allowed to cool, upon which gelation or thickening occurs. Cooling may be achieved actively (e.g. by a cooling device) or passively, e.g. by letting it cool to ambient conditions.

Depending upon the exact conditions, cells/droplets of solvent and compound of interest may be entrapped in the gel/thickened solvent or solid particles of the compound of interest may form.

Optionally, solid particles are formed later, e.g. by drying such as freeze-drying.

Heating or cooling may be realized by adding a cooling or heating medium to the solution. For instance, cooling can be achieved by, amongst others, adding a cooler solvent, solid $CO_2$ or a cooling gas.

In an embodiment, the temperature is changed by adding a fluid to the solution of the gelator/thickener, which causes the solution of the gelator/thickener to rise or drop in temperature, thereby causing gelation/thickening. This may suitably be accomplished by adding a fluid of a different temperature to the solution of the thickener/gelator, thereby causing the temperature to change to a temperature at which thickening/gelling occurs. The compound of interest may be in the solution with the thickener/gelator or in the fluid of a different temperature.

For instance, to a solution of the thickener/gelator and the compound of interest in a liquid that dissolves the thickener/gelator at a high temperature but not at a low temperature, another or the same liquid for the thickener/gelator, at a low temperature, is added, thereby lowering the temperature of the solution of the thickener/gelator to a temperature at which gelation or thickening occurs.

Depending upon the choice of the liquids and the compound of interest, particle formation may be effected together with thickening/gelling, if at the temperature at which gelling/thickening occurs the compound of interest is not (fully) soluble in the liquid system.

Particle formation may be effected later. e.g. by drying, such as freeze-drying (see also above).

Of course it is also possible to make use of temperature effects in a method wherein first separate solutions are made of compound of interest and of the gelator/thickener. For instance a solution of the thickener/gelator may be contacted with a solution of the compound of interest, said second solution having a different temperature than the first, leading to a change of the temperature to a value at which gelation/thickening, and optionally particle formation, occurs.

Gelating/Thickening by Concentrating the Gelator/Thickener in the Liquid

In an embodiment gelation/thickening is achieved by concentrating a solution of the gelator/thickener. Concentration may for instance be realized by evaporation of the liquid wherein the gelator/thickener is dissolved. As the solution gets more concentrated, the viscosity will start to increase (thickening). Gelation will occur upon reaching the critical gelation concentration, i.e. the minimal concentration necessary to achieve gelling for a particular system. The concentration by evaporation may proceed to an extent at which particle formation of the compound of interest occurs.

Depending upon the nature of the compound of interest and the liquid, evaporation may cause the solid particles to be formed or may lead to entrapment of cells/droplets comprising liquid and compound of interest. Solid particles may then be formed upon freeze-drying.

Direct Thickening/Gelation from Solid Gelator/Thickener

In a suitable method, an amount of the thickener is brought into contact with a solution of the compound of interest in a solvent, which is a non-solvent for the thickener/gelator. In time gelation or thickening occurs.

In order to facilitate gelation it has been found advantageous to apply sonication.

Depending upon the nature of the compound of interest and the liquid, evaporation may cause the solid particles to be formed or may lead to entrapment of cells/droplets comprising liquid and compound of interest. Solid particles may then be formed upon freeze-drying.

Adding the Compound of Interest after Gelling/Thickening

In a suitable method, to a thickened solution or gel comprising the thickener/gelator, a solution of the compound of interest in a solvent wherein the thickener/gelator does not (fully) dissolve, may be added. The solvent may be the same or different as the liquid used in the gel.

The addition may be done by allowing the solution of the compound of interest to diffuse into the gel or it could be stirred or sprayed into the gel. The skilled person will know how to choose suitable conditions. Formation of solid particles may be carried out later, e.g. by freeze-drying.

By choosing a solvent for the compound of interest wherein the compound of interest does not fully dissolve anymore after addition to the gel (e.g. as a result of a temperature change, a pH change), formation of solid particles may be effected during addition.

Depending upon the ratio gel/thickened solution to solution of the compound of interest particle formation of the compound of interest may be effected as a direct result of the addition, in particular if this ratio is relatively high. In particular this can be effected by choosing the ratio such that an uptake (absorption) of the solvent of the compound of interest by the gel/thickened solution takes place, thereby effectively concentrating the compound of interest in the solution of the compound of interest. As the concentration increases above its solubility, solid particles are formed. The skilled person will know how to choose suitable conditions, based upon the information described herein, common general knowledge and optionally a limited amount of routine experimentation.

Use of a Pro-thickener/Pro-gelator

In a suitable method, to a solution of the compound of interest and of a pro-thickener/pro-gelator (by pro-thickener/pro-gelator is meant a molecule that by means of a trigger, chemical or physical, can be transformed into a thickener/ gelator) in a solvent, which is a non-solvent for the thickener/gelator, a trigger is applied, upon which gelation or thickening occurs.

In particular, the trigger may be a chemical that can induce a pH change leading to the formation of the thickener/gelator (examples of such pro-gelators/pro-thickeners and their triggers can e.g. be found in: S. R. Haines et al. *Chem. Commun.* 2002, 2846-2847; K. J. C. van Bommel et al. *Angew. Chem. Int. Ed.* 2004, 43, 1663-1667), an exchange of ions leading to the formation of the thickener/gelator (B. Messersmith et al. *J. Am. Chem. Soc.* 2001, 123, 9463-9464), a reaction leading to the formation of the thickener/gelator (R. P. Lyon et al. *J. Am. Chem. Soc.* 2001, 123, 4408-4413), a reaction leading to the incorporation of the chemical in the thickener/gelator (R. G. Weiss et al. *Langmuir* 2002, 18, 7124-7135), a non-covalent interaction leading to the formation of the thickener/gelator (N. Boden et al. *Angew. Chem. Int. Ed.* 2003, 42, 5603-5606), an enzyme that can induce a pH change leading to the formation of the thickener/gelator, an enzyme that can induce a reaction leading to the formation of the thickener/gelator. Light (S. Shinkai et al. *J. Am. Chem. Soc.* 1994, 116, 20-32), temperature and electrochemical stimuli are also considered triggers.

In a suitable method, to a solution of a pro-thickener/pro-gelator in a solvent which is a non-solvent for both the compound of interest and the thickener/gelator, the compound of interest is added and a trigger is applied, upon which the pro-thickener/pro-gelator becomes the thickener/gelator and the non-solvent becomes a solvent for the compound of interest and remains a non-solvent for the thickener/gelator, therefore gelation or thickening occurs. For this embodiment a trigger causing a change in pH has been found particularly suitable.

In a suitable method, to a solution of the compound of interest and of a pro-thickener/pro-gelator in a solvent, which is a non-solvent for the thickener/gelator, a trigger is applied, upon which the pro-thickener/pro-gelator becomes the thickener/gelator and the solvent becomes a non-solvent for the compound of interest and gelation or thickening occurs. For this embodiment a trigger causing a change in pH has been found particularly suitable.

In the above methodologies amounts and nature of liquids such as solvents, non-solvents, gelators/thickeners, compounds of interest can suitably be determined by the skilled person based upon common general knowledge, the information described herein and, optionally, a limited amount of routine experimentation.

Any of the measures suitable for inducing gelation/thickening and/or particle formation may be combined. The skilled person will know how to choose suitable conditions (such as solvents, concentrations, temperatures, pH values, etc.)

Many variations are possible wherein the effect of temperature is used, as will be appreciated by the skilled person. The skilled person will also appreciate that in analogous manner use can be made of other triggers to initiate particle formation and gelling/thickening, such as a variation in the pH.

The skilled person will appreciate that in all the cases where particles of the compound of interest are not formed during the methods described above, particle formation can still occur if the described formulation is then dried e.g. freeze-dried or spray-dried. These particles can be particles of the compound of interest as such or coated with gelator, or they can be mixed particles of gelator and compound of interest. Particle formation can also occur when the formulation is delivered, for example by means of oral delivery to an animal or a person, and changes occur to the formulation when inside the body (e.g. changes in pH along the gastrointestinal tract).

When the same solvent is used for gelator/thickener and compound or interest, use of a temperature effect has been found to be very suitable to induce thickening/gelation.

Using only one solvent instead of more has been found easier with respect to solvent removal, if solvent removal is desired. Such solvent may for instance very suitably be an organic solvent or an aqueous solution at a pH at which both the drug and the gelator or thickener dissolve.

After thickening/gelling, the thickened solution/gel may be used as such or the particles of the compound of interest may be isolated from the thickened solution or gel.

Suitable isolation methods are known in the art, and the skilled person will know how to select such a method, for a specific type of particles and thickened solution/gel.

A method wherein the isolation is effected by reversing the thickening or gelation without re-dissolving the precipitated particles has been found very suitable. This can suitably be realized by using a solvent wherein the thickener/gelator dissolves and the particle does not. The thickening/gelation may also be reversed in another way, for instance by changing the pH, by heating the gel/thickened solution, by sonication, by irradiation with light (if a light sensitive thickener/gelator is used) or by a chemical reaction capable of either changing the physical conditions within the gel or capable of reacting with the gelator/thickener in such a way that it becomes a non-gelator/non-thickener. Examples of suitable chemical inducers for triggering gel-to-sol or sol-to-gel formation are disulfide reducing enzymes and thiol oxidizing enzymes, which in nature also occur in the human body. Also tris-(2-carboxy ethyl)phosphine, mercaptoethanol, 1,4-dithiothreitol, glutathione and dimethyl sulfoxide (DMSO) can be used for chemical triggering. Examples of suitable triggering methods are e.g. described in WO 03/084508.

The skilled person will know how to choose suitable conditions based on common general knowledge and the information disclosed in the present description and claims.

Figure 8:
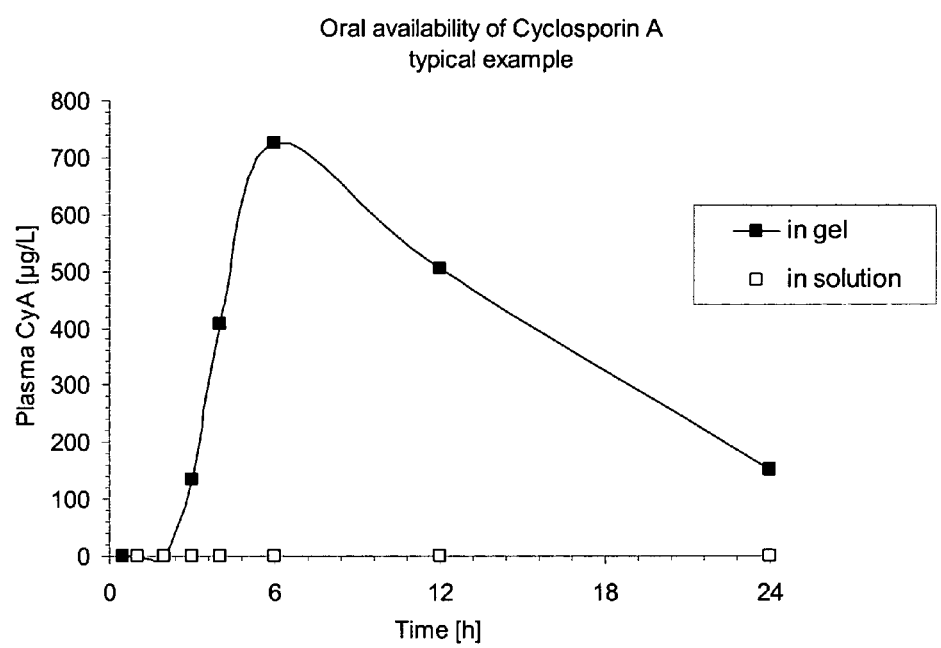
FIG. 8 shows a diagram displaying the oral availability of Cyclosporin A obtained by using a gel formulation of cHexAm(PheAmBn)(CH$_2$CH$_2$OCH$_2$CH$_2$OH)$_2$ gelator (black squares) and in a reference formulation without gelator (white squares).

The invention further relates to particles of a compound of interest, preferably a pharmaceutically or biologically active compound, obtainable by a method according to any of the preceding claims. It has been found that a particulate material obtainable in accordance with the invention shows a favorable oral availability pattern that is distinct from particles obtained in a conventional method (see e.g. FIG. 8; Example 17).

Preferably particles according to the invention have a particle size in the range of from 1 nm to 100 µm, more preferably in the range of from 1 to 250 nm, even more preferably in the range of from 1-100 nm.

Particles of the invention, especially nano-particles, have been found to have very satisfactory dissolution behavior. In particular, it has been found that a particle according to the invention has an improved bioavailability compared to a particle prepared with a conventional method. More in particular, this has been found the case for a particle obtainable by a method involving the use of a gelator/thickener according to Formula I, II or III.

The invention allows for the formation of crystalline, amorphous or semi-crystalline particles.

The invention will now be illustrated by the following Examples.

Example 1

Figure 4:
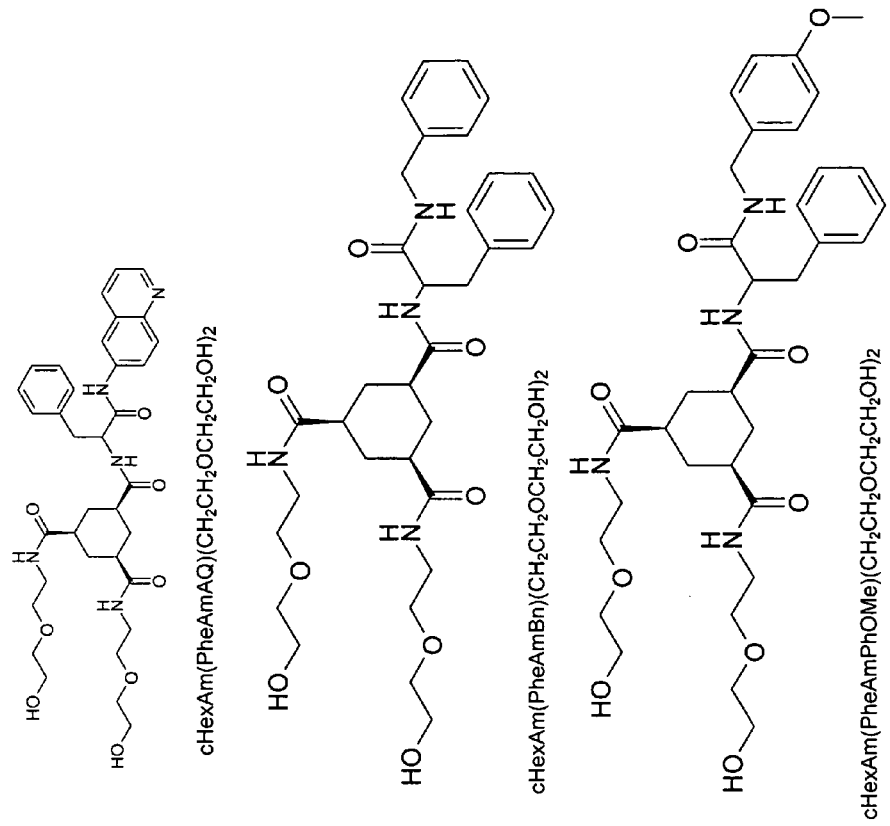
FIG. 4 shows the chemical structures of some gelators which may be used in accordance with the invention.
Figure 4:
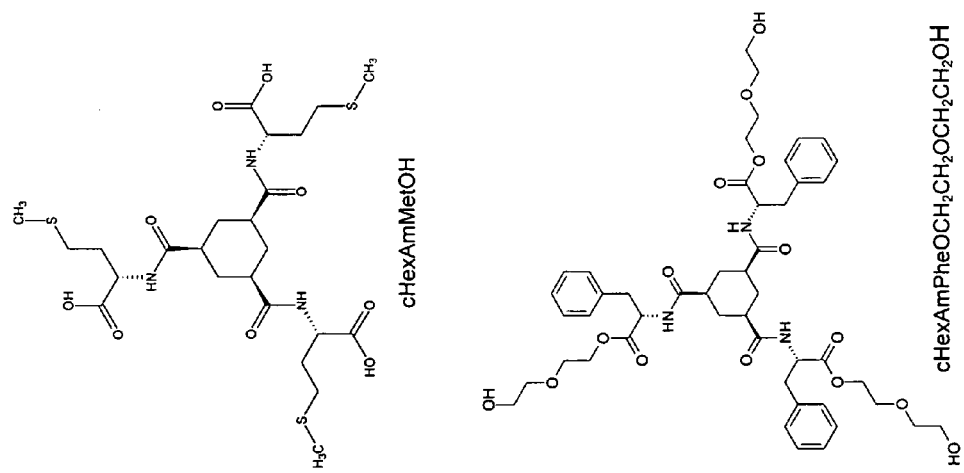

To a solution containing 5 mg ($8.2 \times 10^{-3}$ mmol) of cHex-AmMetOH gelator (see FIG. 4 for structure) and 1.66 mg ($8.2\times10^{-3}$ mmol) of pyrene in 100 μL of DMSO, 900 μL of distilled water were quickly added. The addition of water resulted in the immediate and complete gelation of the solution. Transmission electron microscopy (TEM) analysis of the gel shows the presence of gel fibres and pyrene particles, the latter with number average size between 14 and 30 nm.

Example 2

To a solution containing 5 mg ($5.4\times10^{-3}$ mmol) of cHexAmPheOCH$_2$CH$_2$OCH$_2$CH$_2$OH gelator(see FIG. 4 for structure) and 1.10 mg ($5.4\times10^{-3}$ mmol) of pyrene in 100 μL of DMSO, 900 μL of distilled water were quickly added. The addition of water resulted in the immediate and complete gelation of the solution. TEM analysis of the gel shows the presence of gel fibres and pyrene particles, the latter with average size between 10 and 60 nm.

Example 3

To a solution containing 4 mg ($6.0\times10^{-3}$ mmol) of cHexAm(PheAQ)(CH$_2$CH$_2$OCH$_2$CH$_2$OH)$_2$ gelator (see Example 12 for the synthesis of this gelator and FIG. 4 for the structure) and 1.22 mg ($6.0\times10^{-3}$ mmol) of pyrene in 100 μL of DMSO, 900 μL of distilled water were quickly added. The addition of water resulted in the immediate and complete gelation of the solution. TEM analysis of the gel shows the presence of gel fibres and pyrene particles, the latter with average size between 37 and 185 nm.

Example 4

Figure 2:
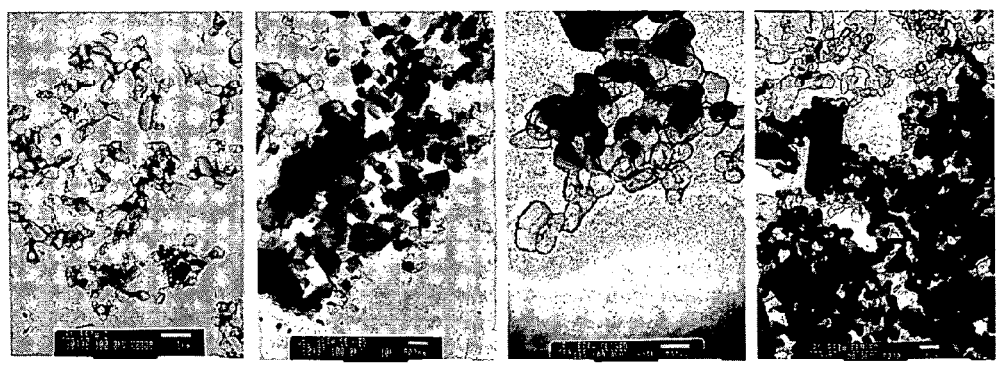
Figure 3:
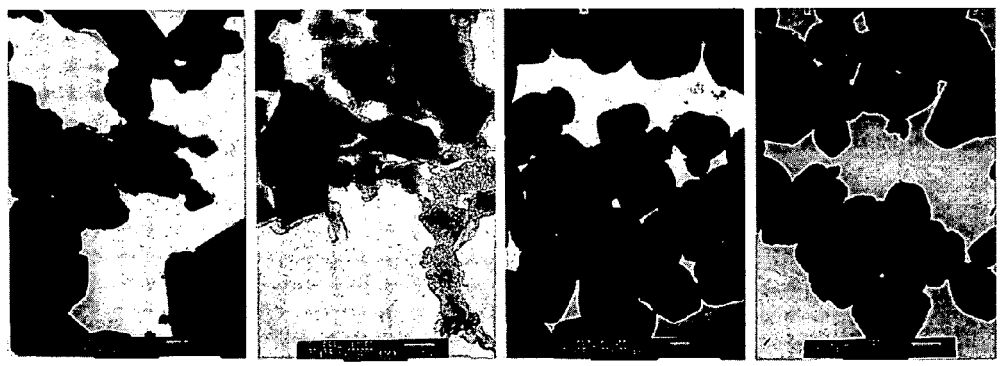
FIG. 3 shows TEM pictures of pyrene ($6.0\times10^{-3}$ mmol), in DMSO/H$_2$O (100 μL/900 μL), examined after 7 days, 18 days, 1 month and 2 months, respectively, from left to right.

To determine the stability in time of pyrene particles in a gel, samples were prepared as in Example 3 and examined with TEM after 7 days, 18 days, 1 month and 2 months. As reference, samples containing only pyrene in DMSO/H$_2$O (100 μL/900 μL) were also prepared. Moreover, to determine the effect of the gelator in solution, i.e. not of the gel, samples containing 4 mg ($6.0\times10^{-3}$ mmol) of cHexAm(PheAQ)(CH$_2$CH$_2$OCH$_2$CH$_2$OH)$_2$ gelator, 1.22 mg ($6.0\times10^{-3}$ mmol) of pyrene, 100 μL of DMSO and 900 μL of 1N HCl were prepared. The presence of HCl causes the gelator to dissolve and therefore the sample remains a solution. All samples were kept at room temperature, in the dark. TEM results are shown in FIGS. 1, 2 and 3. FIG. 1: after 7 days only very few particles, 37-185 nm, are present in the sample; after 18 days more particles, 30-190 nm, can be observed; after 1 month also some crystals, ~150 nm, can be observed; after 2 months more crystals with sizes ranging from 80 to 200 nm are present. FIG. 2: after 7 days crystals, 0.2-3 μm, can be observed; after 18 days more of such crystals can be observed; after 1 month also larger crystals, 6 μm, can be seen; after 2 months more of such crystals can be observed. FIG. 3: after 7 days, 18 days or 1 month crystals, 0.4 to 9 μm, are present; after 2 months crystals, 2-12 μm, can be observed.

Example 5

To a solution containing 4.6 mg ($7.6\times10^{-3}$ mmol) of cHexAmMetOH gelator and 1.3 mg ($3.8\times10^{-3}$ mmol) of danazol in 100 μL of DMSO, 900 μL of distilled water were quickly added. The addition of water resulted in the immediate and complete gelation of the solution. TEM analysis of the gel shows the presence of gel fibres and of rod-shaped danazol particles 0.2 to 1.7 μm wide and 1-10 μm long. In a reference sample consisting only of danazol in 100 μL of DMSO and 900 μL of distilled water, rod-shaped danazol particles are 0.5-10 μm wide and 15-53 μm long.

Example 6

To a solution containing 7 mg ($7.6\times10^{-3}$ mmol) of cHexAmPheOCH$_2$CH$_2$OCH$_2$CH$_2$OH gelator and 1.3 mg ($3.8\times10^{-3}$ mmol) of danazol in 100 μL of DMSO, 900 μL of distilled water were quickly added. The addition of water resulted in the immediate and complete gelation of the solution. TEM analysis of the gel shows the presence of gel fibres and of danazol particles, 0.6×0.6 μm, and rod-shaped particles 0.2-0.6 μm wide and 0.6-6 μm long. In a reference sample consisting only of danazol in 100 μL of DMSO and 900 μL of distilled water, rod-shaped danazol particles are 0.5-10 μm wide and 15-53 μm long.

Example 7

Example 6 was repeated but with an increased molar ratio of gelator to danazol, of 5:1. TEM analysis showed the presence of gel fibres and of danazol particles, the latter with an average size of 20 nm, some particles were approximately 200 nm, and almost no rod-shaped danazol particles were present.

Example 8

To a solution containing 1.96 mg ($2.9\times10^{-3}$ mmol) of cHexAm(PheAQ)(CH$_2$CH$_2$OCH$_2$CH$_2$OH)$_2$ gelator and 1.0 mg ($2.9\times10^{-3}$ mmol) of danazol in 50 μL of DMSO, 950 μL of distilled water were quickly added. The addition of water resulted in the immediate and complete gelation of the solution. TEM analysis of the gel shows the presence of gel fibres and of danazol particles, the latter with average size between 140-700 nm, some rod-shaped danazol particles 0.7 μm wide and 9 μm long were also present.

In a reference sample consisting only of danazol in 100 μL of DMSO to which 900 μL of distilled water was added, rod-shaped danazol particles were formed, which were 0.5-10 μm wide and 15-53 μm long.

Example 9

Example 8 was repeated with an increased molar ratio of gelator to danazol (from 1:1 to 2:1). TEM analysis showed the presence of gel fibres and of danazol particles, the latter with an average size of 28 nm, some particles were 2 μM and very few particles were 10 μm, no rod-shaped danazol particles were present. When the molar ratio was increased again from 2:1 to 5:1, TEM analysis showed the presence of gel fibres and of danazol particles, the latter with an average size of 14 nm, some particles were 400 nm, and no rod-shaped particles were present.

Example 10

Freeze-drying of a gel containing cHexAmPheOCH$_2$CH$_2$OCH$_2$CH$_2$OH and danazol in a 5:1 molar ratio, in DMSO/water mixture (50 μL/950 μL) yielded a dry powder of gelator and danazol. TEM analysis of this powder showed similar features to the corresponding gel sample (Example 7): gel fibres and danazol particles, the latter with an average size of 20 nm, very few rod-shaped particles approximately 500-900 nm wide were present.

Example 11

Freeze-drying of a gel containing cHexAm(PheAQ)(CH$_2$CH$_2$O CH$_2$CH$_2$OH)$_2$ and danazol in a 5:1 molar ratio, in DMSO/water (50 μL/950 μL) yielded a dry powder of gelator and danazol. TEM analysis of this powder showed similar features to the corresponding gel sample (Example 9): gel fibres and danazol particles, the latter with an average size of 14-70 nm, no rod-shaped particles were present.

Example 12

To 23 mg ($25\times10^{-3}$ mmol) of cHexAmPheOCH$_2$CH$_2$OCH$_2$CH$_2$OH and 4.2 mg ($12.4\times10^{-3}$ mmol) of danazol, 400 μL of propylene glycol (PG) (A), or 300 μL PG and 100 μL water (B), or 200 μL PG and 200 μL water (C), or 100 μL PG and 100 μL PEG400 and 200 μL water (D), or 200 μL PEG400 and 200 μL water (E), or 300 μL PEG400 and 100 μL water (F) were added. The samples were heated till complete dissolution of both the gelator and danazol was achieved and were then allowed to cool and thus gelate. TEM analysis of the gel shows the presence of gel fibres and danazol particles, the latter with number average size between: 19 and 560 nm (A), 15 and 50 nm (B), 37 and 100 nm (C), 185 and 280 nm (D), 28 and 100 nm (E), 22 and 100 nm (F).

Example 13

To 12.5 mg ($20\times10^{-3}$ mmol) of cHexAm(PheAmBn)(CH$_2$CH$_2$OCH$_2$CH$_2$OH)$_2$ (see FIG. 4 for structure) and 1 mg ($0.83\times10^{-3}$ mmol) of cyclosporine A (CyA), 50 μL of propylene glycol (PG), 50 μL PEG400 and 900 μL water were added. The sample was heated till complete dissolution of both the gelator and CyA was achieved and was then allowed to cool and thus gelate. TEM analysis of the gel shows the presence of gel fibres and CyA particles, the latter with number average size between: 40 and 100 nm.

Example 14

Figure 5:
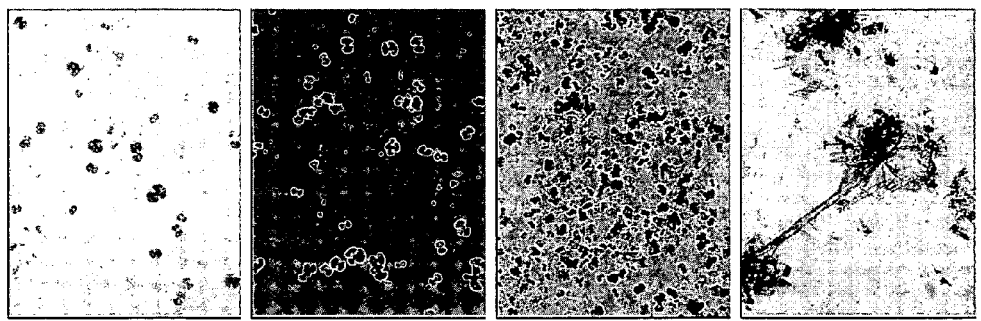
FIG. 5 shows optical microscopy pictures of gels of cHexAm(PheAmBn)(CH$_2$CH$_2$OCH2CH$_2$OH)$_2$ (a), cHexAm(PheAmPhOMe)(CH$_2$CH$_2$OCH2CH$_2$OH)$_2$ (b), cHexAmPheOCH$_2$CH$_2$OCH$_2$CH$_2$OH (c), containing furosemide, and of a solution (d) of furosemide in 50 μL of propylene glycol, 50 μL of PEG400, and 900 μL of water.

Furosemide, 5 mg, ($15\times10^{-3}$ mmol), together with 12.5 mg ($20\times10^{-3}$ mmol) of cHexAm(PheAmBn)(CH$_2$CH$_2$OCH$_2$CH$_2$OH)$_2$ (A), or 12.9 mg ($20\times10^{-3}$ mmol) of cHexAm(PheAmPhOMe)(CH$_2$CH$_2$OCH$_2$CH$_2$OH)$_2$ (B), or 18.4 mg ($20\times10^{-3}$ mmol) of cHexAmPheOCH$_2$CH$_2$OCH$_2$CH$_2$OH(C), were dissolved in 50 μL of propylene glycol, 50 μL of PEG400, and 900 μL of water by heating until a clear solution was obtained. As reference, a sample without gelator was prepared (D). Upon cooling, samples (A), (B), and (C) formed a gel. Optical microscopy results of the gels and of the reference solution of the furosemide in propylene glycol, PEG 400 and water (D) are shown in FIG. 5. FIG. 5: (a) butterfly-shaped crystals, ~25 μm (long axis); (b) butterfly-shaped crystals, ~25 μm (long axis); (c) globular crystals, ~25 μm; (d) rod-shaped crystals, 25-250 μm (long axis).

Example 15

Figure 6:
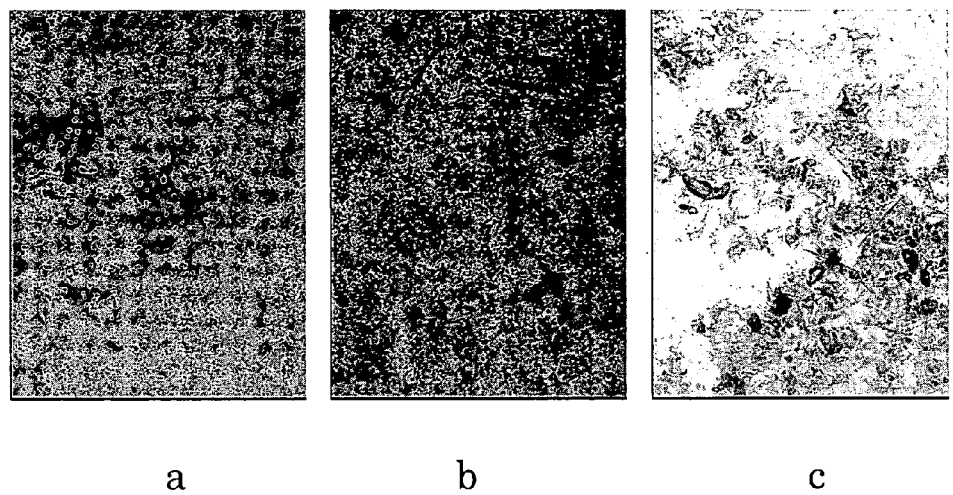
FIG. 6 shows optical microscopy pictures of gels of cHexAm(PheAmAQ)(CH$_2$CH$_2$OCH$_2$CH$_2$OH)$_2$ (a), cHexAmPheOCH$_2$CH$_2$OCH$_2$CH$_2$OH)$_2$ (b) containing danazol, and of a solution (c) of danazol in 100 μL of DMSO, 900 μL of water.

Danazol, 1 mg, ($3\times10^{-3}$ mmol), together with 3.9 mg ($6\times10^{-3}$ mmol) of cHexAm(PheAmAQ)(CH$_2$CH$_2$OCH$_2$CH$_2$OH)$_2$ (A), or 5.4 mg ($6\times10^{-3}$ mmol) of cHexAmPheOCH$_2$CH$_2$OCH$_2$CH$_2$OH (B), were dissolved in 50 μL of DMSO and 950 μL of distilled water by heating until a clear solution was obtained. As reference, a sample without gelator was prepared (C). Upon cooling, samples (A) and (B) formed a gel. Optical microscopy results are shown in FIG. 6. FIG. 6 shows (a) amorphous globular particles, <2 μm; (b) amorphous globular particles, <2 μm and some needle-shaped crystals, 25-50 μm (long axis); (c) rod-shaped crystals, 20-120 μm.

Example 16

Figure 7:
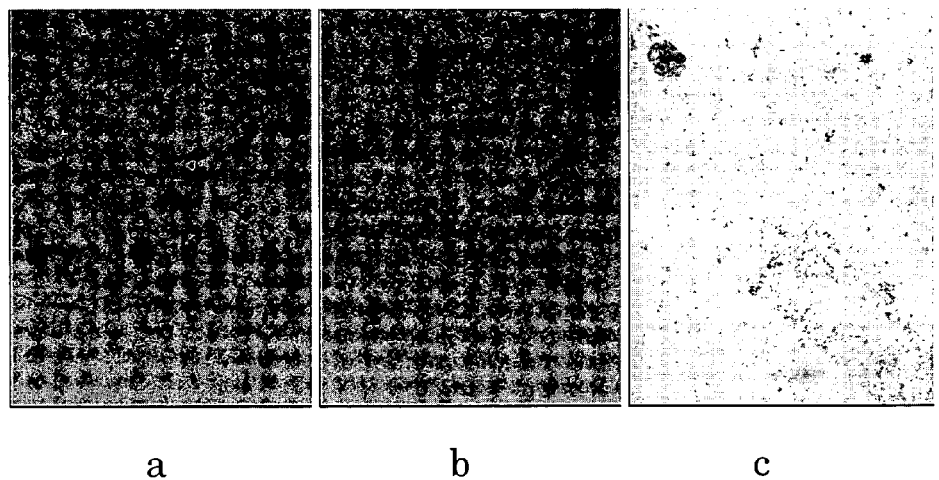
FIG. 7 shows optical microscopy pictures of gels of cHexAm(PheAmBn)(CH$_2$CH$_2$OCH$_2$CH$_2$OH)$_2$ (a), cHexAmPheOCH$_2$CH$_2$OCH$_2$CH$_2$OH (b), containing cyclosporin A, and of a solution (c) of cyclosporin A in 25 μL of propylene glycol, 25 μL of PEG400, and 450 μL of water.

Cyclosporin A, 2.5 mg, ($2.1\times10^{-3}$ mmol), together with 6.3 mg ($10\times10^{-3}$ mmol) of cHexAm(PheAmBn)(CH$_2$CH$_2$OCH$_2$CH$_2$OH)$_2$ (A) or 9.2 mg ($10\times10^{-3}$ mmol) of cHexAmPheOCH$_2$CH$_2$OCH$_2$CH$_2$OH (B), were dissolved in 25 μL of propylene glycol, 25 μL of PEG400, and 450 μL of distilled water by heating until a clear solution was obtained. As reference, a sample without gelator was prepared (C). Upon cooling, samples (A) and (B) formed a gel. Optical microscopy results are shown in FIG. 7. FIG. 7: (a) amorphous globular particles, <2 μm; (b) amorphous globular particles, <2 μm; (c) amorphous globular particles, <2 μm and amorphous aggregates, ~50 μm.

Example 17

In Vivo Testing

The bioavailability of Cyclosporin A (CyA) obtained with the use of a gel was compared to that from the same formulation without gelator. The gel formulation consisted of 5 mg CyA and 9 mg cHexAm(PheAmBn)(CH$_2$CH$_2$OCH$_2$CH$_2$OH)$_2$ gelator in a 1 ml solution of PG:PEG400:water, prepared as in Example 13. The formulations were given by oral gavage to conscious male Wistar rats that had been fasted overnight. The rats remained deprived of food till 4 hours after administration of the CyA sample. Blood was taken at the depicted time-points (see FIG. 8) via a permanent cannula in the jugular vein till 24 hours after the start of the experiment. No detectable amounts of CyA (detection limit of 25 μg/L) were found in the blood when the CyA was administered in the ungelated form. In contrast, when the CyA was administered in the gel formulation, CyA was recovered in the blood, with a maximal concentration between 600 and 900 μg/L after 4 to 6 hours.

This experiment was repeated with several other pharmaceutically active compounds, and also showed an improvement in the oral bioavailability.

Example 18

Synthesis of cHexAm(PheAmAQ)(CH$_2$CH$_2$OCH$_2$CH$_2$OH)$_2$

Step 1. Synthesis of cHex(AmPheAmQ)(COOH)$_2$

To a solution of cis,cis-1,3,5-cyclohexanetricarboxylic acid (11.18 g; 51.71 mmol) and HOBT (2.55 g, 18.87 mmol) in DMSO (200 mL) was added CDI (2.80 g, 17.27 mmol). After stirring for 2 h at RT, Phe-6AQ.2HBr (4.51 g, 10.0 mmol) and Et$_3$N (4.04 g, 40.0 mmol) were added and stirring was continued overnight after which the solution was poured into H$_2$O (600 mL), resulting in the formation of a precipitate, that was filtered off. Subsequently it was dissolved in DMSO/H$_2$O/acetone and again filtered, after which the acetone was slowly evaporated, resulting in the formation of a precipitate that was collected by filtration and subsequently dried to give pure cHex(AmPheAmAQ)(COOH)$_2$ as a light orange solid. Yield: 2.95 g (6.03 mmol=60.3%).

Step 2. Synthesis of cHexAm(PheAmQ)(CH$_2$CH$_2$OCH$_2$CH$_2$OH)$_2$

A solution of cHex(AmPheAmAQ)(COOH)$_2$ (2.80 g, 5.73 mmol), 2(-2-aminoethoxy)-1-ethanol (1.36 g, 12.94 mmol), and DMT-MM (3.58 g, 12.94 mmol) in MeOH (100 mL) and DMSO (60 mL) was stirred overnight at RT. After completion of the reaction H$_2$O (300 mL) was added and the resultant precipitate was filtered off, washed with H$_2$O (3×100 mL), and dried. The crude product was purified by column chromatography (SiO$_2$, CH$_2$Cl$_2$:MeOH=9:1-8:2) to give pure cHexAm(PheAmAQ)(CH$_2$CH$_2$OCH$_2$CH$_2$OH)$_2$ as a light yellow solid. Yield: 1.60 g (2.41 mmol=42.1%).

Gel test: 0.3 mg/mL in H$_2$O or PBS: clear gel; 0.5 mg/mL in H$_2$O/DMSO (19:1): clear gel; 0.6 mg/mL in H$_2$O/EtOH (19:1): clear gel; 25 mg/ml in EtOH: gel.

Example 19

Synthesis of cHexAm(PheAmBn)(CH$_2$CH$_2$OCH$_2$CH$_2$OH)$_2$

Step 1. Synthesis of cHex(AmPheAmBn)(COOH)$_2$

This compound was synthesized according to the procedure described for cHex(AmPheAmAQ)(COOH)$_2$ in Example 18, using PheAmBn-TFA (4.00 g, 9.88 mmol) and Et$_3$N (2.02 g, 20.0 mmol). The solid that was collected by filtration was washed with H$_2$O (3×100 mL) and then extracted with hot MeOH (3×100 mL+3×30 mL). The combined MeOH fractions were evaporated to dryness to give pure cHex(AmPheAmBn)(COOH)$_2$ as a white solid. Yield: 2.00 g (4.4 mmol=44.5%).

Gel test: 3 mg/mL in H$_2$O: gel.

PheAmBn·TFA was synthesized according to: Katritzky, A. R.; Suzuki, K.; He, H.-Y., *J. Org. Chem.* 2002, 67, 8224-8229.

Step 2. cHexAm(PheAmBn)(CH$_2$CH$_2$OCH$_2$CH$_2$OH)$_2$

This compound was synthesized according to the procedure described for cHexAm(PheAmAQ)(CH$_2$CH$_2$OCH2CH$_2$OH)$_2$ in Example 18, using pure cHex(AmPheAmBn)(COOH)$_2$ (2.00 g, 4.4 mmol) in MeOH (120 mL). After completion of the reaction the resultant gelly precipitate was filtered off, washed with MeOH (2×50 mL) and dried to give cHexAm(PheAmBn)(CH$_2$CH$_2$OCH$_2$CH$_2$OH)$_2$ as a white solid. Yield: 1.80 g (2.87 mmol=65.3%).

Gel test: 1.0 mg/mL in H$_2$O: gel; acetone 7.0 mg/mL: clear gel.

Example 20

Synthesis of cHexAm(PheAmPhOMe)(CH$_2$CH$_2$OCH$_2$CH$_2$OH)$_2$

Step 1. Synthesis of cHex(AmPheAmPhOMe)(COOH)$_2$

This compound was synthesized according to the procedure described for cHex(AmPheAmAQ)(COOH)$_2$ in Example 18, using PheAmPhOMe (1.95 g, 7.22 mmol). The solid that was collected by filtration was washed with H$_2$O (3×150 mL) and then extracted with hot MeOH (3×100 mL). The combined MeOH fractions were evaporated to dryness and the resultant solid was recrystallized/regellated from MeOH to give pure cHex(AmPheAmPhOMe)(COOH)$_2$ as a white solid. Yield: 2.85 g (6.1 mmol=84.3%).

Gel test: 3 mg/mL in H$_2$O: clear gel.

PheAmPhOMe was synthesized according to: Fink, C. A.; Carlson, J. E.; Boehm, C.; McTaggart, P.; Qiao, Y.; Doughty, J.; Ganu, V.; Melton, R.; Goldberg, R. *Bioorg. Med. Chem. Lett.* 1999, 9, 195-200.

Step 2. cHexAm(PheAmPhOMe)(CH$_2$CH$_2$OCH$_2$CH$_2$OH)$_2$

This compound was synthesized according to the procedure described for cHexAm(PheAmAQ)(CH$_2$CH$_2$OCH$_2$CH$_2$OH)$_2$ in Example 18, using cHex(AmPheAmPhOMe)(COOH)$_2$ (0.95 g, 2.03 mmol) in MeOH/DMSO (50/20 mL). After completion of the reaction the resultant gelly precipitate was filtered off, washed with MeOH (10 mL) and dried. The filtrates were added to H$_2$O (300 mL) and the resultant precipitate was filtered off, washed with H$_2$O (3×100 mL) and dried. The combined solids were recrystallized/regellated from MeOH to give cHexAm(PheAmPhOMe)(CH$_2$CH$_2$OCH$_2$CH$_2$OH)$_2$ as a white solid. Yield: 0.76 g (1.18 mmol=58.1%).

Gel test: 3.0 mg/mL in H$_2$O: gel

What is claimed is:

1. A method for producing particles of a compound of interest, said method comprising the steps of:
   providing a first solution comprising the compound of interest in a first solvent;
   inducing thickening or gelation of the first solution by a process comprising the step of adding a low molecular weight thickener or gelator having a molecular weight of less than 5000 g/mol to at least the first solution,
   wherein the thickener or gelator is a thickener and gelator represented by formula I:

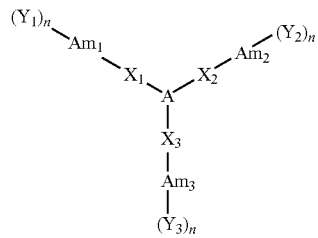

Formula I wherein
   A represents a cycloalkyl, a heterocycloalkyl, an aromatic or heteroaromatic moiety;
   each of $X_1$, $X_2$ and $X_3$ is independently selected from the group consisting of the moieties —N(H)—, —C(O)—, —O(CO)—, —OC(S)—, —C(S)—, —NHC(S)—and —NH—C(O)—;
   each of $Am_1$, $Am_2$, and $Am_3$ is a moiety selected from the group consisting of an amino acid, a derivative of an amino acid, a number of amino acids, and derivatives of a number of amino acids;
   each of $Y_1$, $Y_2$, and $Y_3$ is independently selected from the group consisting of —OR, —N(OH)R, and —NR$_2$, if the corresponding X ($X_1$ for $Y_1$, $X_2$ for $Y_2$, and $X_3$ for $Y_3$) is —(O)— or —NH—C(O)— and n =1, and each of $Y_1$, $Y_2$, and $Y_3$ is independently selected from the group consisting of —C(O)R, —C(O)—NR$_2$, —C(O)—OR, C(S)R, —C(S)—NR$_2$, —C(S)—OR and R, if the corresponding X ($X_1$ for $Y_1$, $X_2$ for $Y_2$, and $X_3$ for $Y_3$) is —NH—and n =1 or 2, wherein each R is independently H, or a substituted or unsubstituted, branched, cyclic or straight alkyl, alkenyl or alkynyl group or wherein each R is independently H, or a substituted or unsubstituted, branched, cyclic or straight alkyl, alkenyl or alkynyl group comprising an aromatic, ester or ether moiety or one or more other heteroatoms and having 1 to 40 carbon atoms; and n is 1 or 2; and
   precipitating the compound of interest in the form of particles upon thickening or gelation of said first solution of the compound of interest with the low molecular weight thickener or gelator.

2. The method according to claim 1, further comprising the step of drying the thickened or gelated first solution by a process selected from the group consisting of freeze-drying, spray-drying, centrifuging, and combinations thereof.

3. The method according to claim 1, further comprising the step of isolating the particles from the thickened or gelated first solution.

4. The method according to claim 3, further comprising the step of reversing the thickening or gelation of the first solution without re-dissolving the precipitated particles.

5. The method according to claim 2, wherein the step of drying the thickened or gelated first solution induces precipitation of the compound of interest.

6. The method according to claim 1, wherein the thickener or gelator is dissolved in the first solution.

7. The method according to claiml, wherein the thickener or gelator is added to said first solution in the form of a second solution in a second solvent, wherein the second solvent is different from the first solvent of the first solution in which the compound of interest is dissolved.

8. The method according to claim 1, wherein gelation or thickening is induced by the presence of a first solvent and/or a second solvent in which the gelator or thickener is essentially not soluble.

9. The method according to claim 8, wherein the solvent in which the gelator or thickener is essentially not soluble is the first solvent in which the compound of interest is dissolved.

10. The method according to claim 8, wherein the gelator or thickener is essentially not soluble in the second solvent, which is different from the first solvent in which the compound of interest is dissolved and which is added to the first solution.

11. The method according to claim 7, wherein the compound of interest is essentially insoluble in the second solvent.

12. The method according to claim 1, wherein the compound of interest is selected from the group consisting of pharmaceuticals, peptides, nucleic acids, proteins, enzymes, growth factors, steroids, hormones, antibiotics, gene therapy agents, catalysts, adsorbents, pigments, coatings, personal care products, abrasives, particles for sensors, metals, alloys, ceramics, membrane materials, nutritional substances, anticancer agents, fertilizers, pesticides, herbicides, and combinations thereof.

13. The method according to claim 12, wherein the compound of interest is a biologically or pharmaceutically active compound.

14. The method according to claim 12, wherein the compound of interest has a low solubility in water.

15. The method according to claim 1, wherein the thickener or gelator is selected from the group consisting of organogelators, comprising hydroxylated carboxylic fatty acids, the amides of carboxylic acids, N, N-dibenzoyl-L-cystine, ureido derivatives, N-acyl amino acids and derivatives, amines of steroids, amides of steroids, and sorbitols.

16. The method according to claim 1, wherein each Y is independently selected from the group consisting of —OH, —O—$(CH_2)_i$—OH, —$NH_2$ —NH$(CH_2)_i$O$(CH_2)_j$OH, —O$(CH_2)_i$O$(CH_2)_j$OH, —NHOH and —NH$(CH_2)_i$OH, wherein i and j are independently 1, 2, 3, 4, 5, 6, 7, or 8.

17. A method for producing particles of a compound of interest, said method comprising:
providing a first solution comprising the compound of interest in a first solvent;
inducing thickening or gelation of the first solution by a process comprising the step of adding a low molecular weight thickener or gelator having a molecular weight of less than 5000 g/mol to at least the first solution, wherein the thickener or gelator is a non-symmetrical, trisubstituted cyclic thickener or gelator selected from Formula II or Formula III,

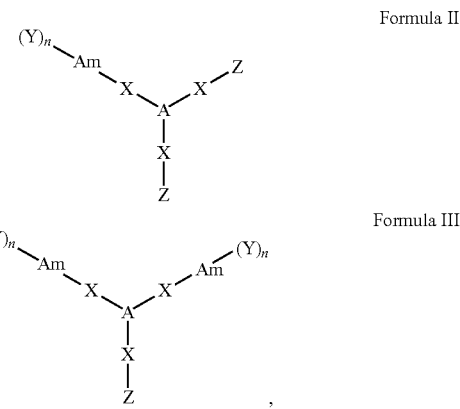

wherein A represents a cycloalkyl, a heterocycloalkyl, an aromatic or heteroaromatic moiety;
each of $X_1$, $X_2$ and $X_3$ is independently selected from the group consisting of the moieties —N(H)—, —C(O)—, —O(CO)—, —OC(S)—, —C(S)—, —NHC(S)— and —NH—C(O)—;
said cyclic thickener or gelator is substituted by at least one X—Am—$Y_n$ groups and at least one other substituent is —X—Z groups wherein
each X is independently selected from the group consisting of —N(H)—, —C(O)—, —OC(S)—, —C(S)—, —NHC(S)—and —NH—C(O)—;
each Am is a moiety selected from the group consisting of an amino acid, a derivative of an amino acid, a number of amino acids, and derivatives of a number of amino acids;
each Y is independently selected from the group consisting of —OR, —N(OH)R, —$NR_2$—C(O)R, —C(O)—$NR_2$, —C(O)OR, —C(S)R, —C(S)—$NR_2$ —C(S)—OR and R, wherein each R is independently defined as in claim 1
each Z is independently selected from the group consisting of —OH, —COOH, —C(O)NHR, —NHC(O)R and —NHR, wherein each R is independently defined as in claim 16; and n=1 or 2; and
precipitating the compound of interest in the form of particles upon thickening or gelation of the first solution of the compound of interest with the low molecular weight thickener or gelator.

18. The method according to claim 1, wherein $X_i$, $X_2$, and $X_3$, are each independently selected from the group consisting of —N(H)—, —C(O)—, —O(CO)—, and —NH—C(O)—.

19. The method according to claim 1, wherein the thickener or gelator is selected from the group consisting of a 1,3,5-substituted cyclohexane, a 1,3,5-substituted benzene, a 1,3,5-substituted cyclohexane wherein all three substituents are in an equatorial plane, and a 1,3,5-substituted benzene wherein all three substituents are in an equatorial plane.

20. The method according to claim 17, wherein —X—Z is selected from the group consisting of —COOH, —C(O)—$NH_2$, —C(O)—$NHCH_3$, —C(O)—NH—$(CH_2)_2$—OH, —C(O)—NH—$(CH_2)_2$—O—$(CH_2)_2$—OH, and C(O)NH$CH_2$-pyr.

21. The method according to claim 1, wherein each Y is independently selected from the group consisting of —OCH$_3$, —OCH$_2$CH$_3$, —NHCH$_2$CH$_2$OCH$_2$CH$_3$, —OCH$_2$CH$_2$OCH$_2$CH$_3$, —NHCH$_3$, —NHCH$_2$CH$_3$, —NH(CH$_2$)$_2$CH$_3$, —NHCH$_2$Ph, —NIT-Ph-O—CH$_3$, —O—naphthyl, —NH—naphthyl, and —NH—quinoline.

22. The method according to claim 1, wherein each Am is independently selected from the group consisting of leucine, isoleucine, lysine, valine, proline, methionine, glycine, histidine, alanine, phenylalanine, tryptophan, serine, threonine, cysteine, tyrosine, asparagine, glutamine, aspartic acid, glutamic acid, arginine, and derivatives thereof.

23. The method according to claim 1, wherein the gelator or thickener cross-links during the induction of thickening or gelation.

24. The method according to claim 1, wherein the first solution is gelled and the gelation of the first solution is induced at the step of adding the gelator to the first solution.

25. The method according to claim 1, wherein the compound of interest is dissolved in a solvent selected from the group consisting of aromatic hydrocarbons, non-aromatic hydrocarbons, alcohols, ethers, esters, aldehydes, ketones, alkanoic acids, epoxides, amines, amides, halogenated hydrocarbons, silicon oils, vegetable oils, phosphoric acids, sulfoxides, nitriles, water, and mixtures of any thereof.

26. The method according to claim 25, wherein the first solvent is selected from the group consisting of water, DMF, NMP, DMSO, ethanol, acetonitrile, propylene glycol and polyethylene glycol.

27. The method according to claim 7, wherein the second solvent is selected from the group consisting of aromatic hydrocarbons, non-aromatic hydrocarbons, alcohols, ethers, esters, aldehydes, ketones, alkanoic acids, epoxides, amines, amides, halogenated hydrocarbons, silicon oils, vegetable oils, phosphoric acids, sulfoxides, nitriles, water, and mixtures of any thereof.

28. The method according to claim 1, wherein thickening or gelation of the first solution and/or second solution is aided by sonication, a chemical trigger, a pH change, a temperature change, light or by adding a non-solvent for the gelator/thickener.

29. The method according to claim 1, wherein thickening or gelation of the first solution and/or second solution is aided by increasing the amount of thickener or gelator in the first solution and/or the second solution.

30. The method according to claim 1, wherein a third solution containing the compound of interest is added to a thickened or gelated solution of the thickener or gelator.

31. The method according to claim 1, wherein the thickener or gelator, the compound of interest, and the first solvent and/or the second solvent are brought into contact with each other in a first solution and/or a second solution, said method further comprising the steps of
raising the temperature of the first solution and/or the second solution, dissolving the compound of interest in the first solution and/or the second solution, and
cooling the resultant solution to at least a temperature wherein the resultant solution is at least partially thickened or gelated.

32. The method according to claim 23, wherein the thickener or gelator comprises a cross-linkable reactive group selected from the group consisting of a —C═C— group or a —SH group.

33. The method according to claim 17, wherein $X_1$, $X_2$, and $X_3$, are independently selected from the group consisting of —N(H)—, —C(O)—, —O(CO)—, and —NH—C(O)—.

34. The method according to claim 17, wherein the thickener or gelator is selected from the group consisting of a 1,3,5-substituted cyclohexane, a 1,3,5-substituted benzene, a 1,3,5-substituted cyclohexane wherein all three substituents are in an equatorial plane, and a 1,3,5-substituted benzene wherein all three substituents are in an equatorial plane.

35. The method according to claim 17, wherein each Y is independently selected from the group consisting of —OCH$_3$, —OCH$_2$CH$_3$, —NHCH$_2$CH$_2$OCH$_2$CH$_3$, —OCH$_2$CH$_2$OCH$_2$CH$_3$, —NHCH$_3$, —NHCH$_2$CH$_3$, —NH(CH$_2$)$_2$CH$_3$, —NHCH$_2$Ph, —NIT-Ph-O—CH$_3$, —O—naphthyl, —NH—naphthyl, and —NH—quinoline.

36. The method according to claim 17, wherein each Am is independently selected from the group consisting of leucine, isoleucine, lysine, valine, proline, methionine, glycine, histidine, alanine, phenylalanine, tryptophan, serine, threonine, cysteine, tyrosine, asparagine, glutamine, aspartic acid, glutamic acid, arginine, and derivatives thereof.

* * * * *